US008269058B2

(12) United States Patent
McCarthy et al.

(10) Patent No.: US 8,269,058 B2
(45) Date of Patent: Sep. 18, 2012

(54) ABSORBABLE TISSUE DRESSING ASSEMBLIES, SYSTEMS, AND METHODS FORMED FROM HYDROPHILIC POLYMER SPONGE STRUCTURES SUCH AS CHITOSAN

(75) Inventors: Simon McCarthy, Portland, OR (US); Barbara McGrath, Portland, OR (US); Ervelyn Winata, Beaverton, OR (US)

(73) Assignee: HemCon Medical Technologies, Inc., Portland, OR (US)

( * ) Notice: Subject to any disclaimer, the term of this patent is extended or adjusted under 35 U.S.C. 154(b) by 686 days.

(21) Appl. No.: 12/218,568

(22) Filed: Jul. 16, 2008

(65) Prior Publication Data
US 2009/0018479 A1  Jan. 15, 2009

Related U.S. Application Data

(63) Continuation-in-part of application No. 11/485,886, filed on Jul. 13, 2006, which is a continuation-in-part of application No. 11/020,365, filed on Dec. 23, 2004, now abandoned, which is a continuation-in-part of application No. 10/743,052, filed on Dec. 23, 2003, now Pat. No. 7,371,403, which is a continuation-in-part of application No. 10/480,827, filed as application No. PCT/US02/18757 on Jun. 14, 2002, now Pat. No. 7,482,503.

(60) Provisional application No. 60/959,641, filed on Jul. 16, 2007.

(51) Int. Cl.
*A61F 13/00* (2006.01)

(52) U.S. Cl. ............... 602/41; 602/44; 602/48; 602/56
(58) Field of Classification Search ............ 602/41–54
See application file for complete search history.

(56) References Cited

U.S. PATENT DOCUMENTS

| | | | |
|---|---|---|---|
| 2,610,625 A | 9/1952 | Sifferd et al. |
| 2,858,830 A | 11/1958 | Robins |
| 2,923,664 A | 2/1960 | Cook et al. |
| 3,551,556 A | 12/1970 | Kliment et al. |
| 3,632,754 A | 1/1972 | Balassa |
| 3,800,792 A | 4/1974 | McKnight et al. |
| 3,801,675 A | 4/1974 | Russell |
| 3,849,238 A | 11/1974 | Gould et al. |
| 3,902,497 A | 9/1975 | Casey |
| 3,911,116 A | 10/1975 | Balassa |
| 3,954,493 A | 5/1976 | Battista et al. |
| 3,977,406 A | 8/1976 | Roth |
| 4,040,884 A | 8/1977 | Roth |
| 4,056,103 A | 11/1977 | Kaczmarzyk et al. |

(Continued)

FOREIGN PATENT DOCUMENTS
EP  0353972  2/1990
(Continued)

OTHER PUBLICATIONS

Allan et al., "Biomedical Applications of Chitin and Chitosan." Chitin, Chitosan, and Related Enzymes—Accademic Press, Inc.: 119-133, 1984.

(Continued)

*Primary Examiner* — Michael A. Brown
(74) *Attorney, Agent, or Firm* — Miller Nesh LLP

(57) ABSTRACT

Absorbable tissue dressing assemblies are formed from hydrophilic polymer sponge structures, such as chitosan.

11 Claims, 11 Drawing Sheets

U.S. PATENT DOCUMENTS

| | | | |
|---|---|---|---|
| 4,068,757 A | 1/1978 | Casey | |
| 4,094,743 A | 6/1978 | Leuba | |
| 4,195,175 A | 3/1980 | Peniston et al. | |
| 4,292,972 A | 10/1981 | Pawelchak et al. | |
| 4,373,519 A | 2/1983 | Errede et al. | |
| 4,394,373 A | 7/1983 | Malette et al. | |
| 4,452,785 A | 6/1984 | Malette et al. | |
| 4,460,642 A | 7/1984 | Errede et al. | |
| 4,501,835 A | 2/1985 | Berke | |
| 4,524,064 A | 6/1985 | Nambu | |
| 4,532,134 A | 7/1985 | Malette et al. | |
| 4,533,326 A | 8/1985 | Anthony | |
| 4,541,426 A | 9/1985 | Webster | |
| 4,599,209 A | 7/1986 | Dautzenberg et al. | |
| 4,651,725 A | 3/1987 | Kifune et al. | |
| 4,684,370 A | 8/1987 | Barrett | |
| 4,699,135 A | 10/1987 | Motosugi et al. | |
| 4,759,348 A | 7/1988 | Cawood | |
| 4,772,419 A | 9/1988 | Malson et al. | |
| 4,833,237 A | 5/1989 | Kawamura et al. | |
| 4,948,540 A | 8/1990 | Nigam | |
| 4,952,618 A | 8/1990 | Olsen | |
| 4,956,350 A | 9/1990 | Mosbey | |
| 4,958,011 A | 9/1990 | Bade | |
| 4,960,413 A | 10/1990 | Sagar et al. | |
| 4,973,493 A | 11/1990 | Guire | |
| 4,977,892 A | 12/1990 | Ewall | |
| 5,006,071 A | 4/1991 | Carter | |
| 5,024,841 A | 6/1991 | Chu et al. | |
| 5,035,893 A | 7/1991 | Shioya et al. | |
| 5,062,418 A | 11/1991 | Dyer et al. | |
| 5,116,824 A | 5/1992 | Miyata et al. | |
| 5,154,928 A | 10/1992 | Andrews | |
| 5,206,028 A | 4/1993 | Li | |
| 5,254,301 A | 10/1993 | Sessions et al. | |
| 5,300,494 A | 4/1994 | Brode, II et al. | |
| 5,376,376 A | 12/1994 | Li | |
| 5,378,472 A | 1/1995 | Muzzarelli | |
| 5,420,197 A | 5/1995 | Lorenz et al. | |
| 5,454,719 A | 10/1995 | Hamblen | |
| 5,525,710 A | 6/1996 | Unger et al. | |
| 5,597,581 A | 1/1997 | Kaessmann et al. | |
| 5,700,476 A | 12/1997 | Rosenthal et al. | |
| 5,756,111 A | 5/1998 | Yoshikawa et al. | |
| 5,797,960 A | 8/1998 | Stevens et al. | |
| 5,821,271 A | 10/1998 | Roenigk | |
| 5,827,265 A | 10/1998 | Glinsky et al. | |
| 5,836,970 A | 11/1998 | Pandit | |
| 5,858,350 A | 1/1999 | Vournakis et al. | |
| 5,952,618 A | 9/1999 | Deslauriers | |
| 5,961,478 A | 10/1999 | Timmermans | |
| 6,042,877 A | 3/2000 | Lyon et al. | |
| 6,054,122 A | 4/2000 | MacPhee et al. | |
| 6,103,369 A | 8/2000 | Lucast et al. | |
| 6,124,273 A | 9/2000 | Drohan et al. | |
| 6,156,330 A | 12/2000 | Tsukada et al. | |
| 6,162,241 A | 12/2000 | Coury et al. | |
| 6,225,521 B1 | 5/2001 | Gueret | |
| 6,270,515 B1 | 8/2001 | Linden et al. | |
| 6,406,712 B1 | 6/2002 | Rolf | |
| 6,448,462 B2 | 9/2002 | Groitzsch et al. | |
| 6,454,787 B1 | 9/2002 | Maddalo et al. | |
| 6,485,667 B1 | 11/2002 | Tan | |
| 6,486,285 B2 | 11/2002 | Fujita | |
| 6,548,081 B2 | 4/2003 | Sadozai et al. | |
| 6,548,569 B1 | 4/2003 | Williams et al. | |
| 6,552,244 B1 | 4/2003 | Jacques et al. | |
| 6,565,878 B2 | 5/2003 | Schoenfeldt et al. | |
| 6,566,577 B1 | 5/2003 | Addison et al. | |
| 6,599,891 B2 | 7/2003 | North et al. | |
| 6,693,180 B2 | 2/2004 | Lee et al. | |
| 6,726,712 B1 | 4/2004 | Raeder-Devens et al. | |
| 6,855,860 B2 | 2/2005 | Ruszczak et al. | |
| 6,863,924 B2 | 3/2005 | Ranganathan et al. | |
| 6,864,245 B2 | 3/2005 | Vournakis et al. | |
| 6,992,233 B2 | 1/2006 | Drake et al. | |
| 7,371,403 B2 | 5/2008 | McCarthy et al. | |
| 7,402,172 B2 | 7/2008 | Chin et al. | |
| 7,482,503 B2 | 1/2009 | Gregory et al. | |
| 7,546,812 B2 | 6/2009 | Eastin et al. | |
| 7,637,934 B2 | 12/2009 | Mangiardi et al. | |
| 7,820,872 B2 | 10/2010 | Gregory et al. | |
| 7,850,709 B2 | 12/2010 | Cummins et al. | |
| 7,897,832 B2 | 3/2011 | McAdams et al. | |
| 8,063,265 B2 | 11/2011 | Beck et al. | |
| 2001/0045177 A1 | 11/2001 | Harvey et al. | |
| 2002/0161376 A1 | 10/2002 | Barry et al. | |
| 2005/0036955 A1 | 2/2005 | DeGould | |
| 2005/0123581 A1 | 6/2005 | Ringeisen et al. | |
| 2005/0137512 A1* | 6/2005 | Campbell et al. | 602/41 |
| 2005/0147656 A1* | 7/2005 | McCarthy et al. | 424/445 |
| 2005/0240137 A1 | 10/2005 | Zhu et al. | |
| 2006/0004314 A1 | 1/2006 | McCarthy et al. | |
| 2006/0184224 A1 | 8/2006 | Angel | |
| 2006/0211973 A1 | 9/2006 | Gregory et al. | |
| 2007/0021703 A1 | 1/2007 | McCarthy | |
| 2007/0066920 A1 | 3/2007 | Hopman et al. | |
| 2007/0083137 A1 | 4/2007 | Hopman et al. | |
| 2007/0255243 A1 | 11/2007 | Kaun et al. | |
| 2008/0132990 A1 | 6/2008 | Richardson | |
| 2008/0147019 A1 | 6/2008 | Song et al. | |
| 2008/0241229 A1 | 10/2008 | Li et al. | |

FOREIGN PATENT DOCUMENTS

| | | |
|---|---|---|
| EP | 0643963 | 3/1995 |
| JP | 60-142927 | 7/1985 |
| JP | 62-039506 | 2/1987 |
| JP | 63-090507 | 4/1988 |
| JP | 07-116241 | 5/1995 |
| JP | 11-342153 | 12/1999 |
| JP | 2002-233542 | 8/2002 |
| WO | WO 95/05794 | 3/1995 |
| WO | WO 99/02587 | 1/1999 |
| WO | WO 00/56256 | 9/2000 |
| WO | WO 02/102276 | 12/2002 |
| WO | WO 03/047643 | 6/2003 |
| WO | WO 03/079946 | 10/2003 |
| WO | WO 03/092756 | 11/2003 |
| WO | WO 03/101310 | 12/2003 |
| WO | WO 2004/047695 | 6/2004 |
| WO | WO 2004/060412 | 7/2004 |

OTHER PUBLICATIONS

Anema et al., "Potential Uses of Absorbable Fibrin Adhesive Bandage for Genitourinary Trauma." World Journal of Surgery, vol. 25: 1573-1577, 2001.

Bégin et al., "Antimicrobial films produced from chitosan." International Journal of Biological Macromolecules, vol. 26: 63-67, 1999.

Belman et al., "From the Battlefield to the Street." Per declaration submitted in U.S. Appl. No. 10/480,827, dated Dec. 17, 2007, poster presentation was made at the ATACCC Conference, Aug. 2006.

Chan et al., "Comparison of Poly-N-acetyl Glucosamine (P-GlcNAc) with Absorbable Collagen (Actifoam), and Fibrin Sealant (Bolheal) for Achieving Hemostasis in a Swine Model of Splenic Hemorrhage." The Journal of Trauma: 454-458, 2000.

CNN Transcript—3pp., Jun. 8, 2006.

Cole et al., "A pilot study evaluating the efficacy of a fully acetylated poly-N-acetyl glucosamine membrane formulation as a topical hemostatic agent." Surgery, vol. 126, No. 3: 510-517, 1999.

HemCon Manufacturing Materials. Per declaration submitted in U.S. Appl. No. 10/480,827, dated Dec. 17, 2007, materials were submitted as supporting evidence for declaration.

Horesh et al., "Pre-hospital use of the HemCon bandage." Per declaration submitted in U.S. Appl. No. 10/480,827, dated Dec. 17, 2007, poster presentation was made at the WCDEM Conference, May 2007.

Kiley, Kevin, "Department of the Army memo." Jul. 20, 2005.

Kumar, Ravi, "Chitin and chitosan fibres: A review." Bulletin of Material Science: vol. 22, No. 5: 905-915, Aug. 1999.

Luo et al., "The role of poly(ethylene glycol) in the formation of silver nanoparticles." Journal of Colloid and Interface Science, vol. 288: 444-448, 2005.

Malette et al., "Chitosan: A New Hemostatic." The Annals of Thoratic Surgery, vol. 36, No. 1: 55-58, Jul. 1983.

Martin et al., "Medical applications of poly-4-hydroxybutyrate: a strong flexible absorbable biomaterial." Biochemical Engineering Journal, vol. 16: 97-105, 2003.

Mi et al., "Fabrication and characterization of a sponge-like asymmetric chitosan membrane as a wound dressing." . Biomaterials, vol. 22: 165-173, 2001.

Moody, Robin J., "HemCon bandage stakes claim to soldier's kit bag." Portland Business Journal, Nov. 4, 2005.

Ohshima et al., "Clinical Application of Chitin Non-Woven Fabric as Wound Dressing." European Journal of Plastic Surgery, vol. 10: 66-69, 1987.

Ohshima et al., "Clinical application of new chitin non-woven fabric and new chitin sponge sheet as wound dressing." European Journal of Plastic Surgery, vol. 14: 207-211, 1991.

Olsen et al., "Biomedical Applications of Chitin and its Derivatives." Chitin and Chitosan: Proceedings from the 4th International Conference on Chitin and Chitosan, 813-829, 1988.

Percot et al., "Optimization of Chitin Extraction from Shrimp Shells." Biomacromolecules, vol. 4: 12-18, 2003.

Pusateri et al., "Advanced Hemostatic Dressing Development Program: Animal Model Selection Criteria and Results of a Study of Nine Hemostatic Dressings in a Model of Severe Large Venous Hemorrhage and Hepatic Injury in Swine." The Journal of Trauma, vol. 55: 518-526, 2003.

Sandford, Paul A., "Chitosan: Commercial Uses and Potential Applications." Chitin and Chitosan: Proceedings from the 4th International Conference on Chitin and Chitosan, 51-69, 1988.

Sandford et al., "Biomedical Applications of High-Purity Chitosan." Water-Soluble Polymers: Chapter 28: 430-445, 1991.

Sandford, Paul A., "Biomedical Applications of New Forms of Chitin/Chitosan." Chitin Derivatives in Life Science, 12pp., 1992.

Siekman, Philip, "A Shrimp Bandage?" Fortune Small Business, pp. 67-68, 2006.

Sondeen et al., "Comparision of 10 Different Hemostatic Dressings in an Aortic Injury." The Journal of Trauma, vol. 54, No. 2: 280-285, 2003.

Wedmore et al., "A Special Report on the Chitosan-based Hemostatic Dressing: Experience in Current Combat Operations." The Journal of Trauma, vol. 60: 655-658, 2006.

Wilson, J.R., "The Army's Greatest Inventions." U.S. Army Materiel Command, pp. 30-37, 2005.

Park et al., "Platelet derived growth factor releasing chitosan sponge for periodontal bone regeneration." Biomaterials, vol. 21: 153-159, 2000.

* cited by examiner

ABSORBABLE TISSUE DRESSING ASSEMBLIES, SYSTEMS, AND METHODS FORMED FROM HYDROPHILIC POLYMER SPONGE STRUCTURES SUCH AS CHITOSAN

RELATED APPLICATIONS

This application claims the benefit of U.S. Provisional Patent Application Ser. No. 60/959,641, filed Jul. 16, 2007 and entitled "Absorbable Tissue Dressing Assemblies, Systems, and Methods Formed From Hydrophilic Polymer Sponge Structures Such as Chitosan." This application is also a continuation in part of U.S. patent application Ser. No. 11/485,886, filed Jul. 13, 2006, which is a continuation in part of U.S. application Ser. No. 11/020,365 filed on Dec. 23, 2004 now abandoned, entitled "Tissue Dressing Assemblies, Systems, and Methods Formed From Hydrophilic Polymer Sponge Structures Such as Chitosan"; which is a continuation in part of U.S. patent application Ser. No. 10/743,052, filed on Dec. 23, 2003, now U.S. Pat. No. 7,371,403, entitled "Wound Dressing and Method of Controlling Severe Life-Threatening Bleeding"; which is a continuation in part of U.S. patent application Ser. No. 10/480,827, filed on Oct. 6, 2004, now U.S. Pat. No. 7,482,503, entitled "Wound Dressing and Method of Controlling Severe Life-Threatening Bleeding," which was a national stage filing under 37 C.F.R. §371 of International Application No. PCT/U502/18757, filed on Jun. 14, 2002, which are each incorporated herein by reference.

FIELD OF THE INVENTION

The invention is generally directed to tissue dressings applied on a site of tissue injury, or tissue trauma, or tissue access to ameliorate bleeding, fluid seepage or weeping, or other forms of fluid loss, as well as provide a protective covering over the site.

BACKGROUND OF THE INVENTION

HemCon® Bandages made and sold by HemCon Medical Technologies Inc. (Portland, Oreg.) incorporate a chitosan sponge matrix having superior adhesive properties and resistance to dissolution in high blood flow, which make them well suited for stanching of severe arterial blood flow.

There remains a need for improved absorbable hemostatic dressings for temporary internal use (e.g. by application by open or non-invasive procedures, such as laparoscopic procedures) or for implantation, which couple flexibility and ease of use with robustness and longevity required for resisting dissolution during use.

SUMMARY OF THE INVENTION

The invention provides absorbable, supple, and densified tissue dressing assemblies, systems and methods formed from hydrophilic polymer sponge structures, such a chitosan. The absorbable tissue dressing assemblies make possible rapid bleeding control (usually within 1 to 2 minutes) in internal bleeding situations, such as during surgery or as the result of trauma, without using thrombin or other hemostatic agents. The tissue dressing assemblies also provide antibacterial/antiviral protection; biocompatibility; and bioabsorbability. The absorbable tissue dressing assemblies are flexible and conformable to tissue surfaces, and present a low/thin profile (e.g., less than 1 mm). They are able to be cut to a desirable size at the instant of use, and (if desired) they can be removed without tissue injury or re-bleeding by saline soaking. The absorbable tissue dressing assemblies make possible the laparoscopic delivery of hemostatic intervention to control internal bleeding episodes during surgery or as a result of trauma.

One aspect of the invention provides an absorbable tissue dressing assembly comprising a tissue dressing matrix comprising an absorbable hydrophilic polymer material, and a flexible absorbable polymer film backing layer.

The flexible absorbable polymer film backing layer can comprise, e.g., a mesh. The flexible absorbable polymer film backing layer can be selected, e.g., from a group consisting of elastomers composed of aliphatic polyurethanes, hyaluronic acid, hyaluronates, and/or other types of absorbable aliphatic polyesters, or a poly-hydroxyl butyrate material.

The absorbable hydrophilic polymer material can be selected, e.g., from a group consisting of a polyacrylate, an alginate, chitosan, a hydrophilic polyamine, a chitosan derivative, polylysine, polyethylene imine, xanthan, carrageenan, quaternary ammonium polymer, chondroitin sulfate, a starch, a modified cellulosic polymer, a dextran, hyaluronan or combinations thereof. The absorbable hydrophilic polymer material can, e.g., comprise a chitosan material obtained from animal crustacean shells.

In one embodiment, the tissue dressing matrix is sized and configured to define a perimeter edge. In this arrangement, the flexible absorbable polymer film backing layer can be sized and configured to extend beyond the perimeter edge to present a skirt of material to receive suture material or staples.

In one embodiment, the flexible absorbable polymer film backing layer is placed, at least in part, internally within the tissue dressing matrix.

In one embodiment, the tissue dressing matrix can be sized and configured to define an elongated strip having opposite ends, so that the elongated strip can be wrapped around a site. In this arrangement, the flexible absorbable polymer film backing layer can be placed at one opposite end of the elongated strip.

In one embodiment, one or more therapeutic agents can be incorporated into the tissue dressing matrix.

Another aspect of the invention provides a method comprising providing an absorbable tissue dressing assembly as defined in any of the various embodiments identified above, and performing a surgical procedure using the absorbable tissue dressing assembly. The surgical procedure can include, e.g., an abdominal aortic aneurysmectomy (AAA); spleen, liver, kidney, or gallbladder surgeries; open heart/bypass procedures; hysterectomies; total joint arthoplasties, burns and face lifts; radical neck dissections; trauma (gun shot, knife wounds, wound debridement); spinal fusions/laminectomies; bowel/colon resections; radial prostatectomies; and vascular anastomoses.

Another aspect of the invention provides a method of manufacturing an absorbable tissue dressing assembly as defined in any of the various embodiments identified above. The method can include, e.g., subjecting a solution of a chitosan hydrophilic polymer to phase separation by a controlled freezing process, followed by a controlled water removal step by freeze-drying or lyophilization to create the tissue dressing matrix. The method can include, e.g., subjecting the tissue dressing matrix, after freeze-drying or lyophilization, to a densification process. The method can include, e.g., heating the tissue dressing matrix, after densification. The method can include, e.g., subjecting the tissue dressing matrix, after freeze-drying or lyophilization, to a softening process.

Other features and advantages of the invention shall be apparent based upon the accompanying description, drawings, and claims.

DETAILED DESCRIPTION

Although the disclosure hereof is detailed and exact to enable those skilled in the art to practice the invention, the physical embodiments herein disclosed merely exemplify the invention, which may be embodied in other specific structure. While the preferred embodiment has been described, the details may be changed without departing from the invention.

I. Absorbable Tissue Dressing Assembly

A. Overview

Figure 1:
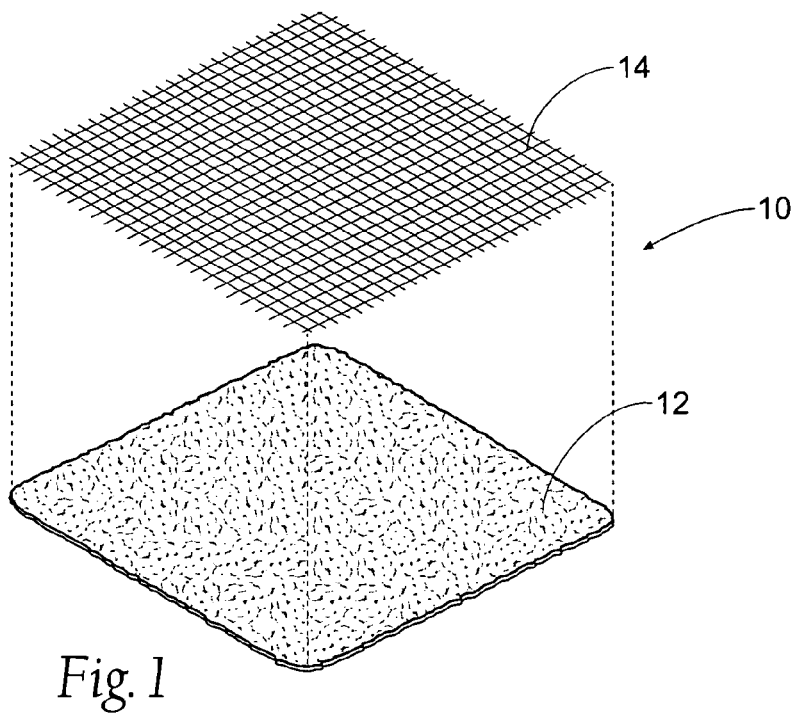
FIG. 1 is a perspective exploded view of a formed hydrophilic sponge material desirably comprising a chitosan matrix, which is sized and figured as a supple, densified tissue dressing assembly.
Figure 2:
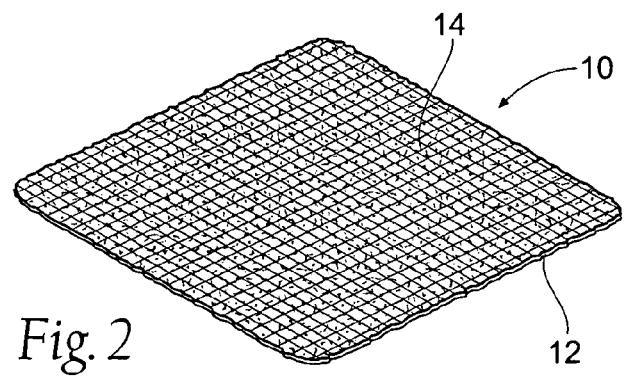
FIG. 2 is a perspective assembled view of the supple, densified tissue dressing assembly shown in FIG. 1.

FIGS. 1 and 2 show a representative embodiment of an absorbable tissue dressing assembly 10 that embodies features of the invention. By "absorbable," it is meant that the assembly 10 is bioabsorbable and/or biodegradable and will, in time after placement within body tissue, be broken down and/or resorbed by the body's natural processes. As shown, the absorbable tissue dressing assembly 10 comprises a relatively thin and supple tissue dressing matrix 12 (shown FIG. 1) comprising a hydrophilic polymer that can be characterized as a supple sponge structure. The absorbable tissue dressing assembly also includes a backing layer 14, which overlays one surface of the tissue dressing matrix 12. Desirably, the tissue dressing matrix 12 and the backing 14 possess different colors (e.g., a standard absorbable dressing indicating violet dye), textures, or are otherwise visually and/or tactilely differentiated, to facilitate recognition by a caregiver.

The absorbable tissue dressing assembly 10 is sized and configured as an adherent, hemostatic dressing for the rapid control of internal bleeding during surgery, in particular when ligature or conventional procedures are ineffective or impractical. The tissue dressing assembly 10 comprises a low profile, highly conformable, adherent sheet, which allows control of local and/or diffuse internal bleeding without the need for clamping or bulky packing. The size, configuration, and mechanical and physical properties of the absorbable tissue dressing assembly 10 make possible the laparoscopic delivery of hemostatic intervention to control internal bleeding episodes during surgery or as a result of trauma, e.g., during laproscopic partial nephrectomy (LPN).

Figure 3:
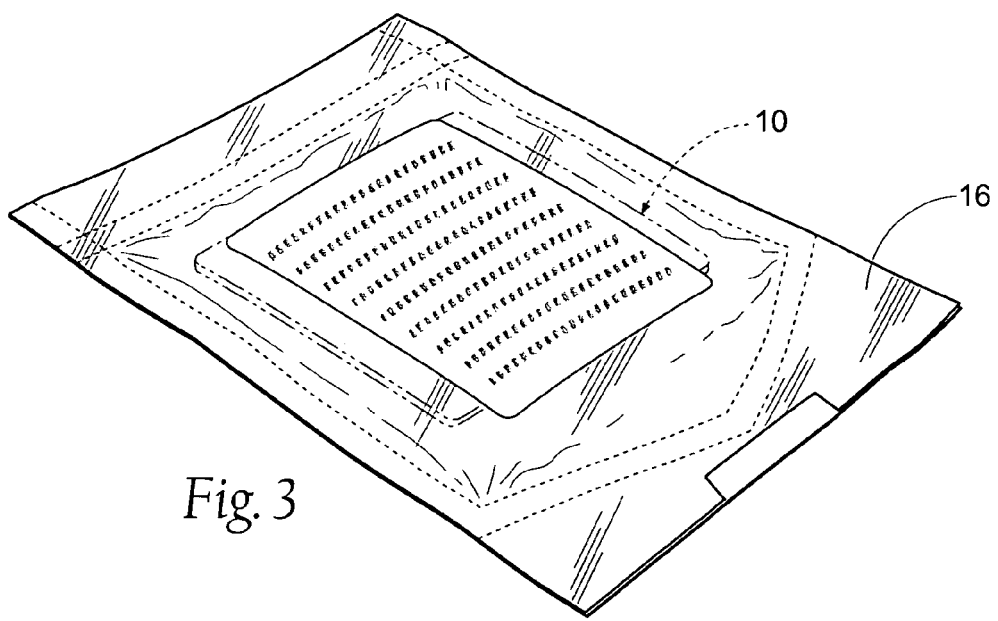
FIG. 3 is a perspective view of a sealed pouch into which the supple, densified tissue dressing assembly shown in FIG. 2 is placed and sterilized prior to use by a caregiver.
Figure 4:
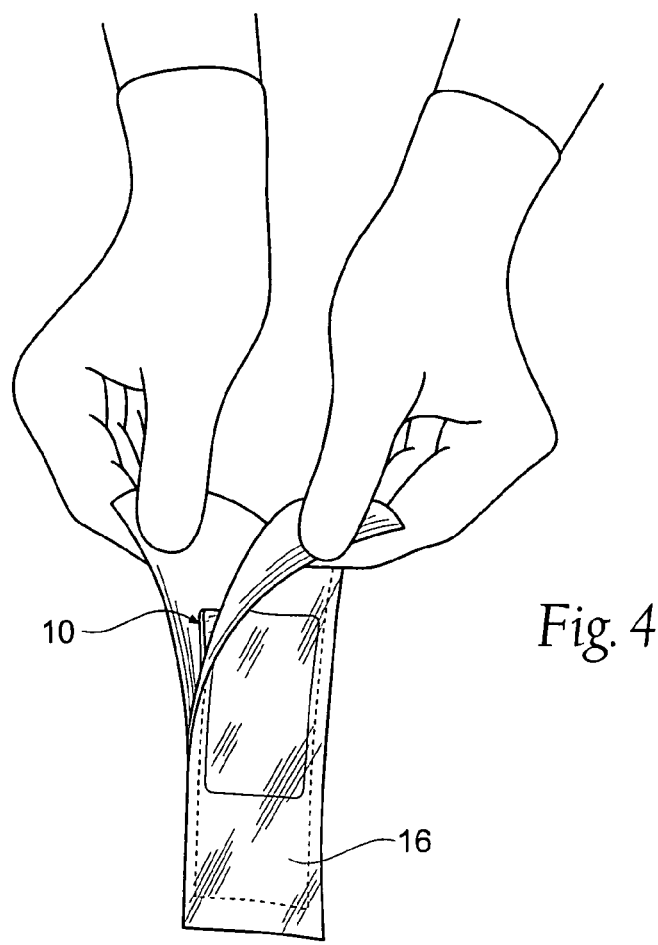
FIG. 4 is a perspective view of the pouch shown in FIG. 3 being opened by a caregiver to gain access to the supple, densified tissue dressing assembly for use.

As FIG. 3 shows, the tissue dressing assembly 10 is desirably vacuum packaged in an air-tight heat sealed foil-lined pouch 16. The tissue dressing assembly 10 is subsequently terminally sterilized within the pouch 16 by use of gamma irradiation. As FIG. 4 shows, the pouch 16 is configured to be peeled opened by the caregiver at the instant of use.

B. The Tissue Dressing Matrix

The tissue dressing matrix 12 desirably includes a hydrophilic polymer material that is selected to actively promote clotting rather than just passively soaking up blood. The hydrophilic polymer is elected to comprise a material that adheres to tissue in the presence of blood, or body fluids, or moisture. The tissue dressing assembly 10 can thus be used to stanch, seal, and/or stabilize a surgical bleeding site against bleeding, fluid seepage or weeping, or other forms of fluid loss.

The tissue dressing matrix 12 may comprise a hydrophilic polymer material, such as a polyacrylate, an alginate, chitosan, a hydrophilic polyamine, a chitosan derivative, polylysine, polyethylene imine, xanthan, carrageenan, quaternary ammonium polymer, chondroitin sulfate, a starch, a modified cellulosic polymer, a dextran, hyaluronan or combinations thereof. The starch may be of amylase, amylopectin and a combination of amylopectin and amylase.

The biocompatible material of the matrix 12 preferably comprises the non-mammalian material poly [β-(1→4)-2-amino-2-deoxy-D-glucopyranose, which is more commonly referred to as chitosan. The chitosan can be processed in conventional ways from chitin obtained from animal crustacean shells, for example, shrimp. Chitosan is biocompatible and is biodegradable within the body, being broken down into glucosamine, a benign material.

The chitosan matrix 12 presents a robust, permeable, high specific, positively charged surface. The positively charged surface creates a highly reactive surface for red blood cell and platelet interaction. Red blood cell membranes are negatively charged, and they are attracted to the chitosan matrix 12. The cellular membranes fuse to chitosan matrix 12 upon contact. A clot can be formed very quickly, circumventing immediate need for clotting proteins that are normally required for hemostasis. For this reason, the chitosan matrix 12 is effective for both normal as well as anti-coagulated individuals, and as well as persons having a coagulation disorder like hemophilia. The chitosan matrix 12 also binds bacteria, endotoxins, and microbes, and can kill bacteria, microbes, and/or viral agents on contact. The chitosan matrix 12 is biocompatible. The chitosan matrix 12 is biodegradable within the body and is broken down into glucosamine, a benign substance, in about 4 to 6 months.

Figure 5:
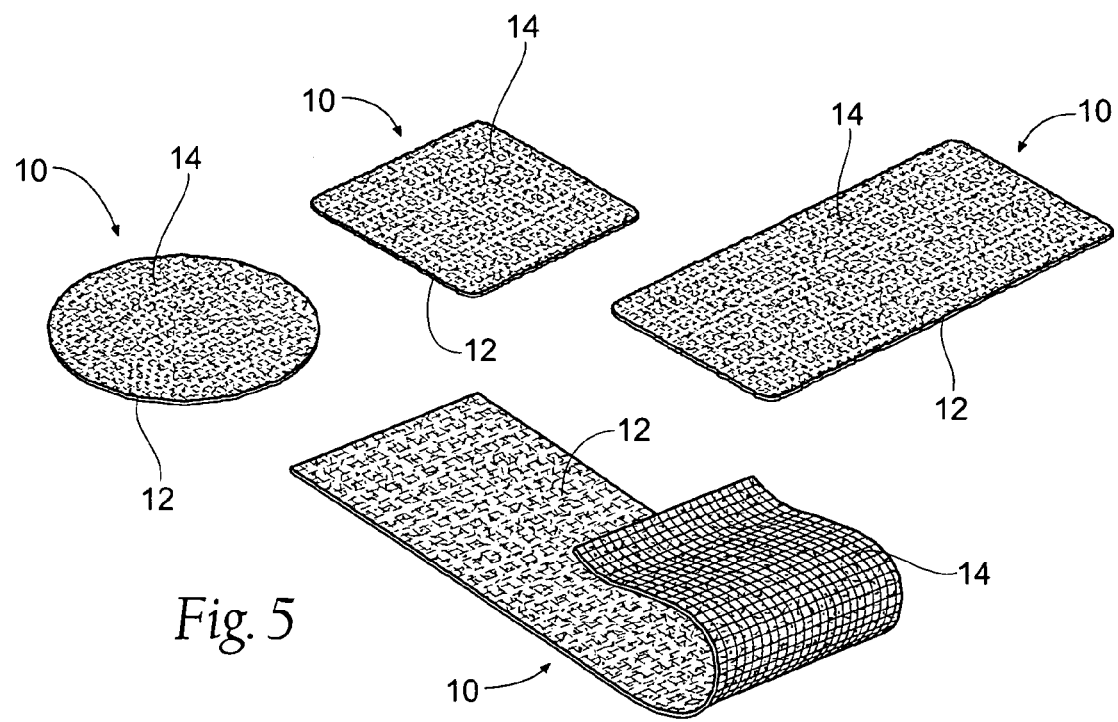
FIG. 5 is a perspective view of the supple, densified tissue dressing assembly formed in different shapes and sizes.
Figure 6:
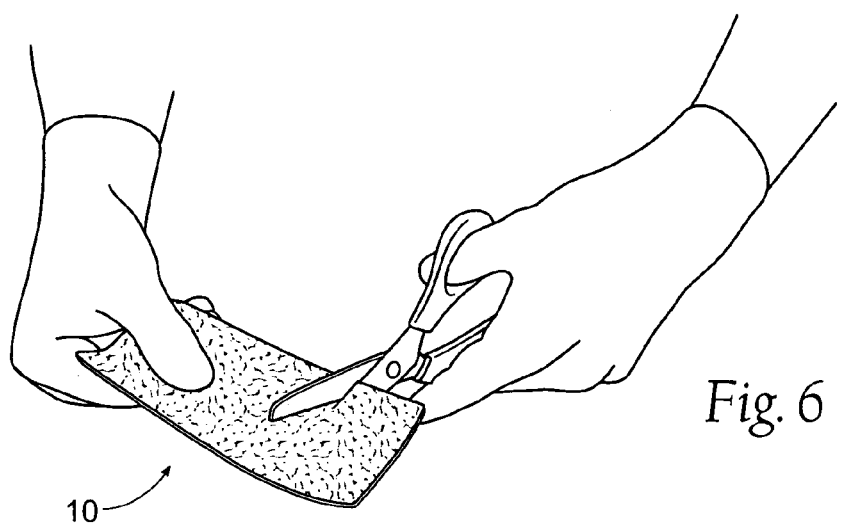
FIG. 6 is a perspective view of the supple, densified tissue dressing assembly being cut to size at the instant of use.

The particular size, shape, and configuration of the tissue dressing matrix 12 can, of course, vary according to its intended use. As will be described in greater detail later, the tissue dressing matrix 12 can be pre-shaped during manufacture. As FIG. 5 shows, the tissue dressing matrix can be formed in various sizes, for example, in round patches 2 to 3 inches in diameter, or in rectilinear patches, e.g., 4 inch by 4 inch, or 2 inch by 2 inch, or 2 inch by 4 inch; or as an elongated strip, which can be cut to size at the instant of use, as FIG. 6 shows.

Figure 7:
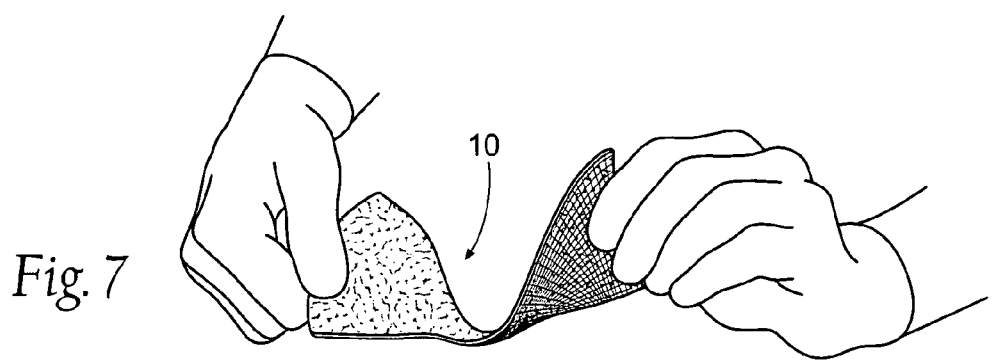
FIG. 7 is a perspective view illustrating how the supple, densified tissue dressing assembly can be flexed, bent, folded, twisted, and even rolled upon itself before and during use, without creasing, cracking, fracturing, otherwise compromising the integrity and mechanical and/or therapeutic characteristics of the matrix.

The thickness of the tissue dressing matrix 12 can also be controlled during manufacture, as will be described in greater detail later. Desirably, the tissue dressing assembly 10 includes a thin and inherently supple chitosan matrix 12 (e.g., between 1.0 mm to 2.0 mm). The suppleness lends compliance and multi-dimensional flexibility. As FIG. 7 shows, the matrix 12 can be flexed, bent, folded, twisted, and even rolled upon itself before and during use, without creasing, cracking, fracturing, otherwise compromising the integrity and mechanical and/or therapeutic characteristics of the matrix 12.

Figure 8:
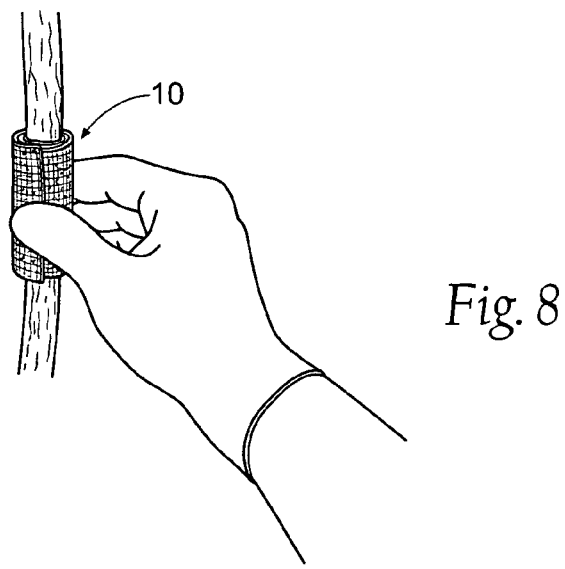
FIG. 8 is a perspective view illustrating how the supply, densified tissue dressing assembly can be wrapped a tissue site, e.g., about a vessel to seal an anastomosis, without collapsing the vessel on itself.

The thin, compliant nature of the matrix 12 provides for optimal ease of application in terms of dressing flexibility and also for optimal likelihood of success in terms of attaching a strong, compliant, hemostatic matrix on or around the application site. The thin, compliant nature of the matrix 12 also makes it possible to wrap the dressing 10 about a site (see FIG. 8) (e.g., about a vessel to seal an anastomosis, or repairing accidental damage to the inferior vena cava during surgery), without collapsing the vessel on itself. A thin, compliant chitosan matrix 12, when dry prior to use, will become rapidly even more compliant when wetted with blood allowing for minimal loading on the vessel or application site during application.

C. The Backing Layer

The absorbable tissue dressing assembly 10 includes a flexible absorbable polymer film or mesh backing layer 14, which is attached to one side of the chitosan matrix 12, e.g., by melt adherence or solution casting. The flexible polymer film or mesh backing layer 14 can be attached or bonded by direct adhesion with a top layer of chitosan matrix 12. Alternatively, an adhesive such as 3M 9942 Acrylate Skin Adhesive, or fibrin glue, or cyanoacrylate glue can he employed.

The flexible polymer film or mesh backing layer 14 provides enhanced mechanical strength and impermeablity to leakage. The flexible polymer film or mesh backing layer 14 also provides an anti-adhesion barrier and a non-adherence outside surface.

The flexible polymer mesh backing layer 14 can include various materials, including, but are not limited to, bio-absorbable, biocompatible elastomers composed of aliphatic polyurethanes, hyaluronic acid, hyaluronates, and/or other types of absorbable aliphatic polyesters, or a poly-hydroxyl butyrate material. The flexible polymer mesh backing layer 14 can comprise a woven material, including a woven nano-fiber material or a woven micro-fiber material. A mesh backing later 14 made from a woven nano-fiber material or a woven micro-fiber material presents an increased surface area that can accelerate biodegradation.

In a representative embodiment, the backing layer 14 comprises poly-4-hydroxy butyrate biomaterial, commercially available as TephaFlex™ Material manufactured by Tepha Inc. In this arrangement, the poly-4-hydroxy butyrate biomaterial comprises a strong, pliable thermoplastic mesh material with a tensile strength of 50 MPa, tensile modulus of 70 MPa, elongation to break of ~1000%, and hardness (Shore D) of 52.8. The poly-4-hydroxy butyrate biomaterial is biocompatible. In vivo, the biomaterial is hydrolyzed to 4-hydroxybutyrate, a natural human metabolite, present normally in the brain, heart, lung, liver, kidney, and muscle. This metabolite has a half-life of just 35 minutes, and is rapidly eliminated from the body (via the Krebs cycle) primarily as expired carbon dioxide.

Figure 9:
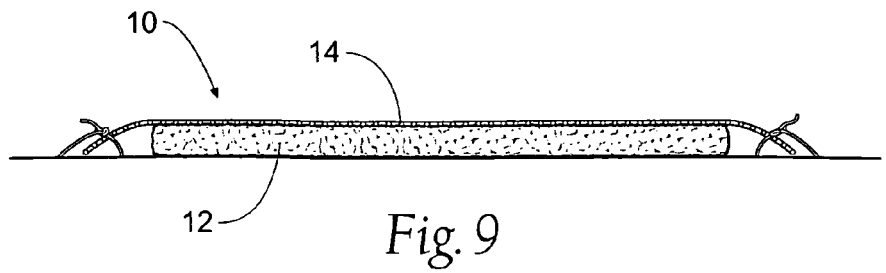
FIG. 9 is a perspective view of an embodiment of a supple, densified tissue dressing assembly having a bio-adsorbable backing layer sized to extend beyond the perimeter of the assembly to present a skirt of material to receive suture material or staples, to stabilize the tissue dressing assembly at the application site.

As FIG. 9 shows, the flexible bio-adsorbable backing layer 14 can be sized to extend beyond the perimeter of the chitosan matrix 12. In this arrangement, the backing layer 14 presents a skirt of material to receive suture material or staples, to stabilize the tissue dressing assembly 10 at the application site. Alternatively, the suture material or staples can be inserted through the chitosan matrix 12 itself.

Figure 10:
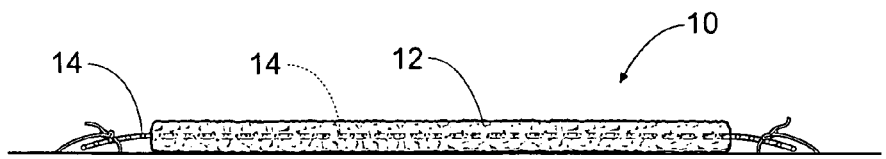
FIGS. 10 and 11 are perspective view of another embodiment of a supple, densified tissue dressing assembly having a bio-absorbable backing placed, at least in part, internally within the assembly, extending beyond the periphery of the assembly (as shown in FIG. 10) to receive suture material or staples, or be placed within the confines of the assembly (as shown in FIG. 11), through which the suture material or staples are passed.
Figure 11:
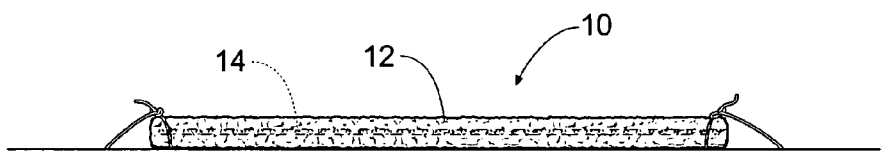

As FIGS. 10 and 11 show, the biomaterial of the backing 14 can be placed, at least in part, internally within the chitosan matrix 12. The material can, like FIG. 9, extend beyond the periphery of the chitosan matrix 12 (as shown in FIG. 10) to receive suture material or staples, or be placed within the confines of the chitosan matrix 12 (FIG. 11), through which the suture material or staples are passed.

Figure 12A:
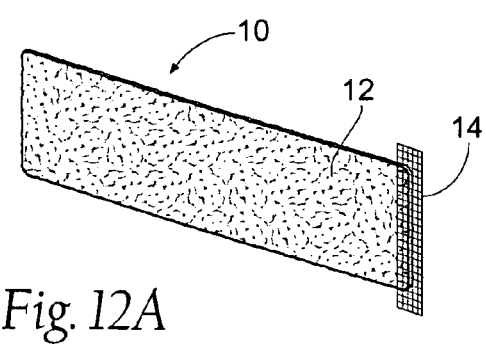
FIGS. 12A and 12B are perspective views of another embodiment of a supple, densified tissue dressing assembly having a strip of biomaterial placed at one end of the assembly (with no such biomaterial at the opposite end of the assembly), which can be used when it is desirable to wrap the tissue dressing assembly in multiple layers around a site, e.g., to seal anastomosis from bleeding (as FIG. 12B shows).
Figure 12B:
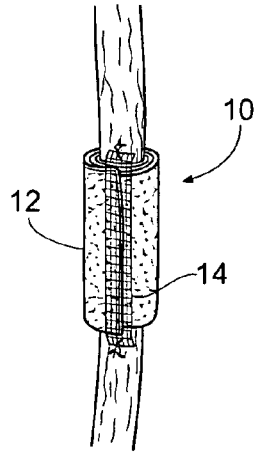

As shown in FIG. 12A, in an alternative embodiment, a strip of the biomaterial of the backing layer can be placed at one end of a thin, elongated chitosan matrix 12, with no such biomaterial at the opposite end of the matrix 12. This arrangement can be used when it is desirable to wrap the tissue dressing assembly 10 in layers around a site, e.g., to seal anastomosis from bleeding or to repair accidental damage to the inferior vena cava during surgery. In this arrangement, the length of the dressing could be designed for use on large vessels with cutting to size of the dressing by a surgeon. The chitosan matrix 12 adheres to itself when wetted with blood and allowing for at least multiple thin layers of encirclement of the anastomosis or vascular repair site by the dressing assembly 10, as FIG. 12B shows.

It should also be appreciated that, for certain indications, an absorbable tissue dressing assembly 10 may be provided without a backing layer. The absence of a backing layer may be advantageous in certain situations, e.g., when stuffing the dressing assembly into a small depressed wound, or when approximating two surface together with a layer of adhesive chitosan between them.

D. Representative Indications

The absorbable tissue dressing assembly 10 can be used during diverse types of surgical procedures with a high incidence of potentially dangerous bleeding, in place of or in association with conventional hemostatic techniques, e.g., use of gauze, sponges, dressings, electrocautery, sutures, ligatures, staples, and sealants.

Illustrative surgical procedures where the absorbable tissue dressing assembly 10 can be used include abdominal aortic aneurysmectomy (AAA); spleen, liver, kidney, or gallbladder surgeries; open heart/bypass procedures; hysterectomies; total joint arthoplasties, burns and face lifts; radical neck dissections; trauma (gun shot, knife wounds, wound debridement); spinal fusions/laminectomies; bowel/colon resections; radial prostatectomies; and vascular anastomoses. The size, configuration, and mechanical and physical properties of the absorbable tissue dressing assembly 10 make possible the laparoscopic delivery of hemostatic intervention to control internal bleeding episodes during surgery or as a result of trauma, e.g., during laproscopic partial nephrectomy (LPN).

II. Manufacture of the Absorbable Tissue Dressing Assembly

A. Overview

As will be described in greater detail later, the hydrophilic polymer matrix 12 is created by subjecting a solution of the chitosan hydrophilic polymer to phase separation by a controlled freezing process, followed by a controlled water removal step by freeze-drying or lyophilization. As will be described in greater detail later, the parameters of the freezing and lyophilization processes are controlled to create a supple sponge-like structure for the chitosan matrix 12. Due to its inherent suppleness, the chitosan matrix 12 is not stiff or brittle. It possesses an inherent capability for flexure and/or twisting without compromising its structural integrity and mechanical and therapeutic properties. As will also be described later, the inherent suppleness of chitosan matrix 12 can also be further enhanced by a mechanical softening process.

As will also be described later, the density of the particular chitosan structure of the matrix 12 following freezing and freeze drying is desirably increased by a mechanical densification process. The mechanical densification process imparts enhanced adhesion strength, cohesion strength and dissolution resistance of the matrix 12 in the presence of blood or body fluids.

B. Representative Manufacturing Process

With reference to FIGS. 13 to 26, a desirable methodology for making the tissue dressing assembly 10 will now be described. It should be realized, of course, that other methodologies can be used.

1. Preparation of a Chitosan Solution

In a preferred embodiment, the matrix 12 comprises poly [$\beta(1\rightarrow 4)$-2-amino-2-deoxy-D-glucopyranose, commonly referred to as chitosan. The chitosan selected for the matrix 12 preferably has a weight average molecular weight of weight of greater than about 60 kDa, and at least about 100 kDa, and more preferably, of at least about 150 kDa. Most preferably, the chitosan has a weight average molecular weight of at least about 300 kDa.

The chitosan used to prepare the chitosan solution preferably has a fractional degree of deacetylation greater than 0.60 but less than 0.97. Most preferably the chitosan has a fractional degree of deacetylation greater than 0.85 but less than 0.95. Preferably the chitosan selected for processing into the matrix has a viscosity at 25° C. in a 1% (w/w) solution of 1% (w/w) acetic acid (AA) with spindle LVI at 30 rpm, which is about 100 centipoise to about 2000 centipoise. More preferably, the chitosan has viscosity at 25° C. in a 1% (w/w) solution of 1% (w/w) acetic acid (AA) with spindle LVI at 30 rpm, which is about 125 centipoise to about 1000 centipoise. Most preferably, the chitosan has viscosity at 25° C. in a 1% (w/w) solution of 1% (w/w) acetic acid (AA) with spindle LV1 at 30 rpm, which is about 300 centipoise to about 850 centipoise.

In forming the matrix 12, the chitosan is desirably placed into solution with an acid, such as citric acid, glutamic acid, lactic acid, formic acid, hydrochloric acid and/or acetic acid. Among these, hydrochloric acid and acetic acid are most preferred, because chitosan acetate salt and chitosan chloride salt resist dissolution in blood whereas chitosan lactate salt and chitosan glutamate salt do not. Larger molecular weight (Mw) anions disrupt the para-crystalline structure of the chitosan salt, causing a plasticization effect in the structure (enhanced flexibility). Undesirably, they also provide for rapid dissolution of these larger Mw anion salts in blood.

The chitosan solution is preferably prepared at 25° C. by addition of water to solid chitosan flake or powder and the solid dispersed in the liquid by agitation, stirring or shaking. On dispersion of the chitosan in the liquid, the acid component is added and mixed through the dispersion to cause dissolution of the chitosan solid. The rate of dissolution will depend on the temperature of the solution, the molecular weight of the chitosan and the level of agitation. Preferably the dissolution step is performed within a closed tank reactor with agitating blades or a closed rotating vessel. This ensures homogeneous dissolution of the chitosan and no opportunity for high viscosity residue to be trapped on the side of the vessel. Preferably the chitosan solution percentage (w/w) is greater than 0.5% chitosan and less than 2.7% chitosan. More preferably the chitosan solution percentage (w/w) is greater than 1% chitosan and less than 2.3% chitosan. Most preferably the chitosan solution percentage is greater than 1.5% chitosan and less than 2.1% chitosan. Preferably the acid used is acetic acid. Preferably the acetic acid is added to the solution to provide for an acetic acid solution percentage (w/w) at more than 0.8% and less than 4%. More preferably the acetic acid is added to the solution to provide for an acetic acid solution percentage (w/w) at more than 1.5% (w/w) and less than 2.5%.

2. Degassing the Aqueous Chitosan Solution

If desired, the chitosan biomaterial may be degassed of general atmospheric gases. Typically, degassing is removing sufficient residual gas from the chitosan biomaterial so that, on undergoing a subsequent freezing operation, the gas does not escape and form unwanted large voids or large trapped gas bubbles in the subject wound dressing product. The degassing step may be performed by heating a chitosan biomaterial, typically in the form of a solution, and then applying a vacuum thereto. For example, degassing can be performed by heating a chitosan solution to about 45° C. immediately prior to applying vacuum at about 500 mTorr for about 5 minutes while agitating the solution.

In one embodiment, certain gases can be added back into the solution to controlled partial pressures after initial degassing. Such gases would include but are not limited to argon, nitrogen and helium. An advantage of this step is that solutions containing partial pressures of these gases form microvoids on freezing. The microvoid is then carried through the sponge as the ice-front advances. This leaves a well defined and controlled channel that aids sponge pore interconnectivity.

3. Freezing the Aqueous Chitosan Solution

The form producing steps for the chitosan matrix 12 are typically carried out from the solution. The form producing steps can he accomplished employing techniques such as freezing (to cause phase separation), non-solvent die extrusion (to produce a filament), electro-spinning (to produce a filament), phase inversion and precipitation with a non-solvent (as is typically used to produce dialysis and filter membranes) or solution coating onto a preformed sponge-like or woven product.

In a preferred embodiment, the chitosan biomaterial—now in acid solution and, if desireds, degassed, as described above—is subjected to a form producing step that includes a controlled freezing process. The controlled freezing process is carried out by cooling the chitosan biomaterial solution within a mold 22.

Figure 13:
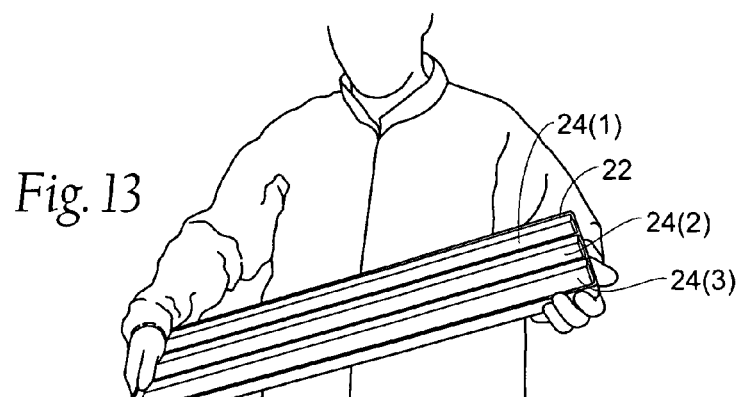
FIG. 13 is a perspective view of a mold in which a hydrophilic sponge material desirably comprising chitosan can be formed by freezing and freeze-drying, and subsequently subject to densification and softening, to form the supple, densified tissue dressing assembly shown in FIG. 1.

The mold 22 can be variously constructed. As shown in FIG. 13, the mold can be made from a metallic material, e.g., Mic 6 aluminum, although other metallic materials and alloys can be used, such as iron, nickel, silver, copper, titanium, titanium alloy, vanadium, molybdenum, gold, rhodium, palladium, platinum and/or combinations thereof.

In a representative embodiment, the mold 22 measures overall 30 inches by 9.8 inches, and is compartmentalized into three mold chambers 24(1), 24(2), and 24(3), each 3 inches in width and 0.051 inch in depth. The mold chambers 24(1), 24(2), and 24(3) are desirably coated with a thin, permanently-bound, fluorinated release coating formed from polytetrafluoroethylene (Teflon), fluorinated ethylene polymer (FEP), or other fluorinated polymeric materials.

Figure 14:
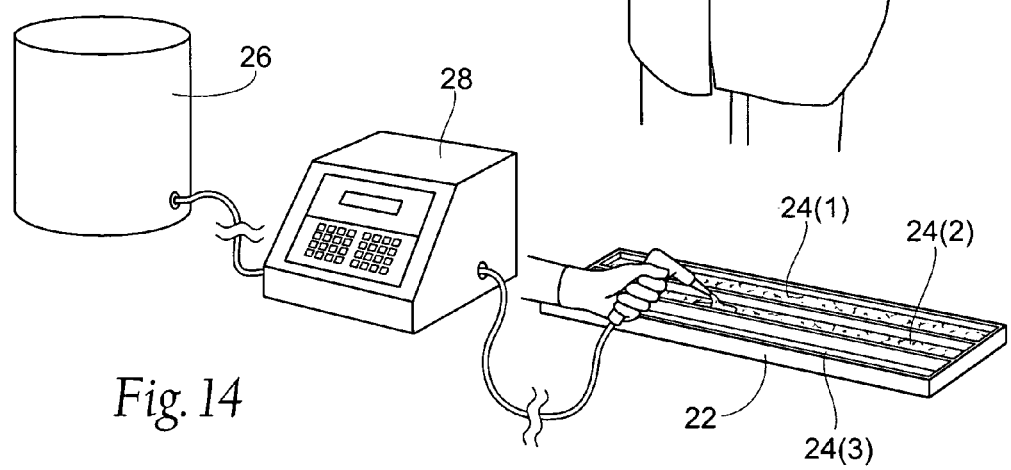
FIG. 14 is a perspective view of a measured volume of chitosan solution being placed into the mold shown in FIG. 13 prior to freezing.

As FIG. 14 shows, a preselected volume of the chitosan biomaterial solution is conveyed from a source 26 into each mold chamber 24(1), 24(2), and 24(3) using, e.g., a positive displacement pump 28. Given the mold dimensions disclosed above, in a representative embodiment, 450 gr +/−13 of chitosan biomaterial solution can be conveyed into each mold chamber 24(1), 24(2), and 24(3). Adding a lesser volume of the chitosan biomaterial solution will result in a matrix that, after molding, possesses a thinner cross section and therefore an ultimately thinner finished matrix 12.

Figure 15:
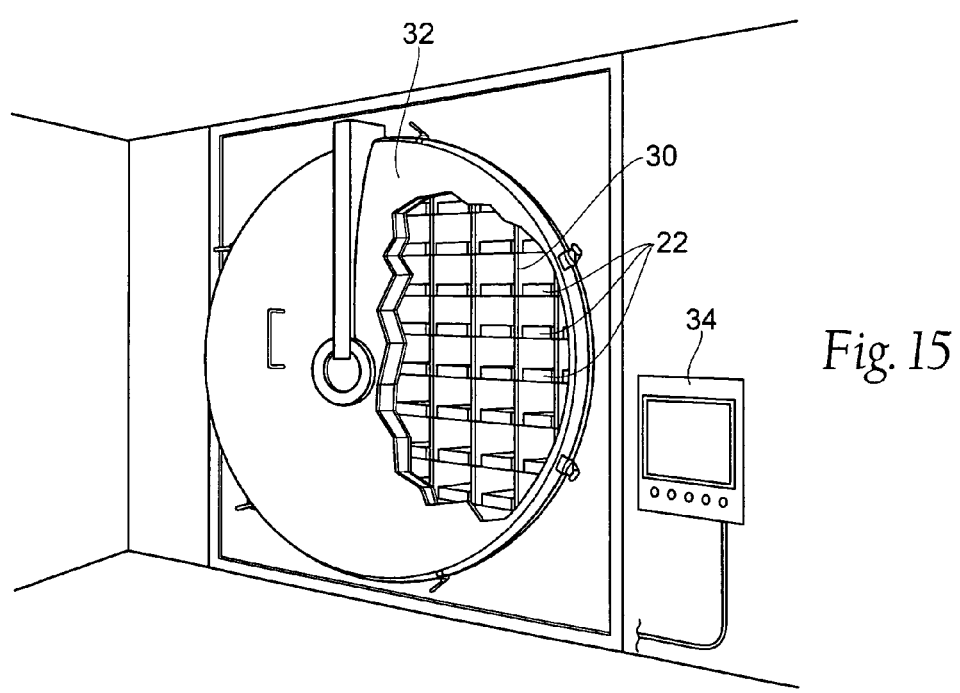
FIG. 15 is a perspective view of a freezer in which the chitosan solution, after having been placed into a mold as shown in FIG. 14, is subjected to a prescribed freezing regime and subsequent freeze drying step.

The mold 22 and chitosan biomaterial solution are then placed in racks 30 within a freezer 32 (FIG. 15). On the racks 30, the bottom of each mold chamber 24(1), 24(2), and 24(3) is placed into thermal contact with a cooling surface. A microprocessor controller 34 carries out the prescribed steps of the freezing process control algorithm.

Within the freezer 32, under the control of the controller 34, the temperature of the chitosan biomaterial solution is ultimately lowered from room temperature (e.g., about 20° C.) to a final temperature well below the freezing point (e.g., minus 40° C.). The chitosan biomaterial solution within each mold chamber 24(1), 24(2), and 24(3) loses heat through the plate cooling surface and ultimately freezes. In this process, the chitosan biomaterial solution undergoes phase separation, which begins to form the desired structure of the matrix.

In a preferred embodiment, during the downward transition in temperatures from room temperature to the final freezing temperature, under the control of the controller 34, the freezing process desirably starts by equalizing the temperatures of the shelf, mold, biomaterial solution, and surrounding air at room temperature and then lowers the temperature of the shelf, mold, biomaterial solution, and air at approximately the same rate to achieve uniform nucleation during phase separation. It is believed that the desired cooling rate to achieve uniform nucleation is less than about 0.5° C./min. It is to be appreciated that the cooling rate is a negative number, because the temperature is dropping from room temperature to a colder freezing temperature. As expressed above, a cooling rate of 1.0° C./min is considered a greater negative rate and therefore not less than a cooling rate of 0.5° C./min. Conversely, a cooling rate of 0.3° C./min is considered a lesser negative rate and therefore is less than 0.5° C./min.

There are various ways for achieving this desired cooling rate and uniformity of temperature conditions among the shelf, mold, biomaterial solution, and air, depending upon the mechanical and operational characteristics and capabilities of the particular freeze dryer 32, e.g., its compressor capability (affecting the cooling rate) and heat flow homogeneity of the cooling chamber.

In a representative embodiment, the desired cooling rate and uniformity of temperature conditions is achieved by including a delay interval. During the delay interval, the controller 34 commands an intermediate temperature condition at a prescribed magnitude above the freezing point, which is held for a prescribed period of time before dropping the temperature to the final freezing temperature.

It has been discovered that imposing a prescribed delay interval in the freezing regime, or otherwise lowering the shelf, mold, biomaterial solution, and air temperature at approximately the same desired cooling rate, results in a supple chitosan sponge structure that is less stiff and brittle, and more readily accommodates flexure without fracturing the sponge structure. In comparison, it has been observed that a freezing regime that transitions temperatures from room temperature to a temperature well below the freezing point, without imposing a delay interval at an intermediate temperature condition above the freezing point, or otherwise lowering the shelf, mold, biomaterial solution, and air temperature at approximately the same desired cooling rate, results in a chitosan sponge structure that is more stiff and brittle, and therefore less able to accommodate extreme flexure without fracturing.

Figure 16A:
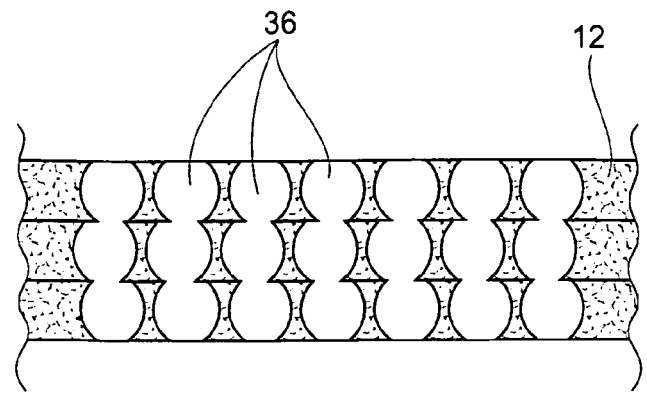
FIG. 16A is a diagrammatic side section view of a desirable chitosan matrix that is formed as a result of the prescribed freezing regime and a subsequent freeze drying step within the freezer shown in FIG. 15, which includes a freezing delay interval.
Figure 16B:
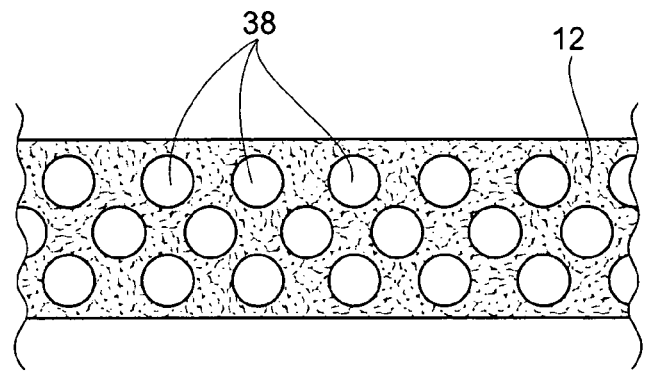
FIG. 16B is a diagrammatic side section view of a chitosan matrix that is formed by a freezing regime and subsequent freeze drying that does not include a freezing delay interval, which results in the creation of a chitosan matrix structure characterized by the presence of unconnected, closed spherolites.

The delay interval produces a preferred structure for the chitosan matrix 12 of a type shown in FIGS. 16A and 16B. This preferred structure is formed by a combined spherulitic and lamella nucleation of crystalline ice and its subsequent phase separation from the other solution components of acid and chitosan.

In the absence of the delay interval and achieving an overall solution cooling rate near or greater than about 0.5° C./min, there is a predominance of lamella structure. Generally it is possible to cause predominant lamella nucleation of ice crystals by preferentially cooling one side of a mold containing a warm aqueous solution such that, with time, all of the solution in the mold is cooled. As the ice crystals form and separate from the solution, individual lamella or sheets of ice grow upward into the cooling solution. On removal of the ice by freeze-drying, the lamella type of nucleation provides for open phase separated structures. Lamella type structures have desirable characteristics, e.g., they are highly permeable; they are easily freeze-dried for rapid removal of ice; they have a relatively large pore size (>20 micron) between lamella; and they can be flexible, depending on lamella orientation. However, lamella type structures are often formed of weakly bound regions that are prone to cracking; lamella type structures can be stiff, depending on lamella orientation; and the specific surface area of lamella type structure can be relatively low.

It has been observed that the resting temperature and time of the delay interval allows for promotion of spherulitically nucleated structure within the lamella structure. Spherulitically nucleated structure both complements and modifies the normal lamella chitosan sponge structure. Spherulitic nucleation of ice is generally caused by uniformly cooling an aqueous solution to below its freezing point so that there is a uniform burst of ice crystals throughout the solution. The advantages of spherulitically nucleation type structures, once freeze dried, include (i) they are highly uniform; (ii) they can have a large specific surface area; (iii) they resist cracking; and (iv) they have uniform strength. The inclusion of the delay interval and the hybrid lamella and spherulitically nucleation type structures that result, provide, after freeze drying, a matrix having improved crack resistance and dressing strength uniformity (i.e., suppleness), while retaining sponge permeability.

Figure 17:
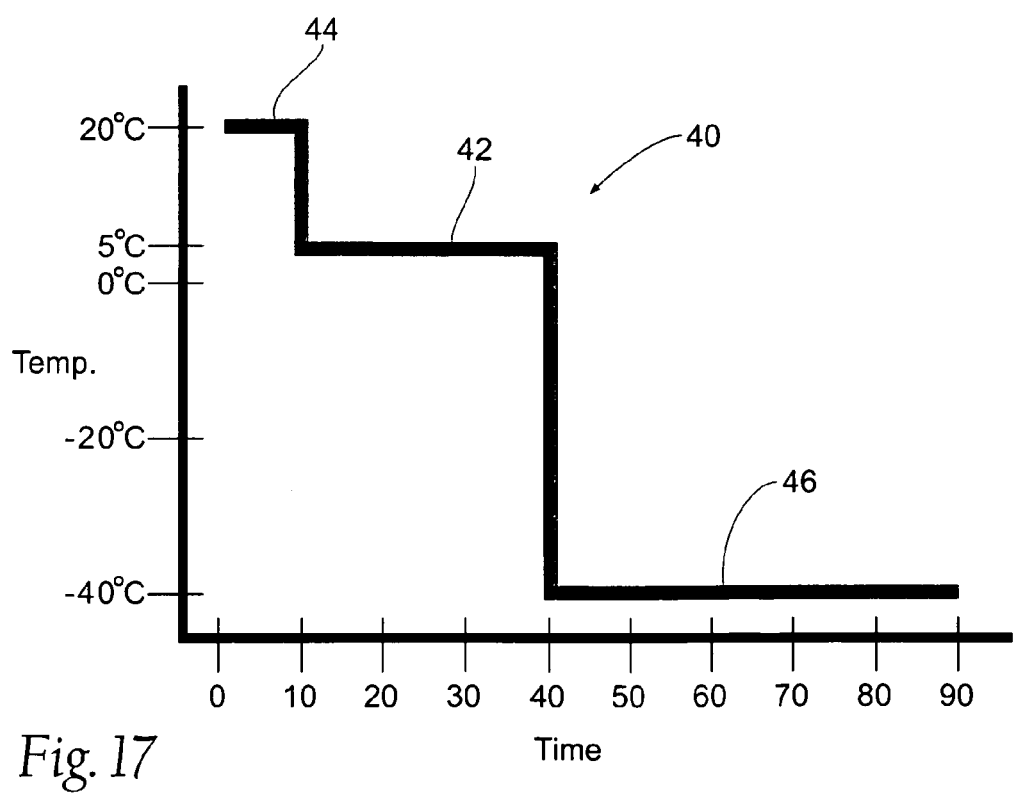
FIG. 17 is a graph showing the phases of a prescribed freezing regime, including a freezing delay interval, that results in the creation of a desirable chitosan matrix structure of the type shown in FIG. 16A.

As shown in FIG. 17, the delayed freezing regime 40 implemented by the controller 34 includes lowering the chitosan biomaterial solution temperature from room temperature to a final temperature below the freezing point, and includes at least one intermediate delay interval 42 that holds a temperature condition for a prescribed period of time at a prescribed increment above the freezing point.

In the illustrated embodiment, the freezing regime 40 includes a first interval 44 that maintains a desired start temperature at or near room temperature (e.g., 20° C.) for a prescribed period of time (e.g., 10 minutes). This assures that the chitosan biomaterial solutions present in all the molds 22 begin the freezing regime 40 at generally the same equilibrium condition.

The freezing regime 40 next drops the temperature to the intermediate temperature, which is held during the delay interval 42. The intermediate temperature is desirably between 2° C. and 10° C. The delay interval 42 is desirably between 20 minutes and 40 minutes. In a representative embodiment, the intermediate temperature is 5° C. and the delay interval 42 is 30 minutes.

It is believed that the delay interval 42 moderates the magnitude of the thermal gradient at the outset of phase separation, as nucleation begins and the spherulites form in the solution. The prescribed intermediate temperature and the duration of delay interval 42 result, at least for a portion of the delay interval 42, in a thermal gradient that approaches zero. In the presence of a low thermal gradient, it is believed that nucleation occurs more uniformly through the volume of chitosan biomaterial solution, allowing adjacent spherulites to form and connect and then open as lamella form, before the chitosan biomaterial solution is exposed to rapid freezing.

The freezing regime 40 includes a final interval 46 that lowers the temperature from the intermediate temperature to the desired final temperature, which is maintained for a prescribed period. In a representative embodiment, the final temperature is minus 40° C., and the prescribed period of time is 50 minutes.

During between each interval 44, 42, and 46 of freezing regime 40, the temperatures may be lowered over a predetermined time period. For example, the freezing temperature of a chitosan biomaterial solution may be lowered from room temperature to the intermediate temperature, or from the intermediate temperature to the final temperature by plate cooling application of a constant temperature cooling ramp of between about −0.4° C./mm to about 0.8° C./mm.

4. Freeze Drying the Chitosan/Ice Matrix

The frozen chitosan/ice matrix desirably undergoes water removal (drying) from within the interstices of the frozen material. This water removal or drying step may he achieved without damaging the structural integrity of the frozen chitosan biomaterial. This may be achieved without producing a liquid phase, which can disrupt the structural arrangement of the ultimate chitosan matrix 12. Thus, the ice in the frozen chitosan biomaterial passes from a solid frozen phase into a gas phase (sublimation) without the formation of an intermediate liquid phase. The sublimated gas is trapped as ice in an evacuated condenser chamber at substantially lower temperature than the frozen chitosan biomaterial. Since the spherulitically nucleated structures that are desirably present within the matrix 12 often retain considerable moisture due to an impermeable shell structure that forms around the ice core, conditions must be maintained during the water removal step to keep the matrix temperature below its collapse temperature, i.e., the temperature at which the ice core within the structure could melt before it is sublimated.

The preferred manner of implementing the water removal step or drying is by freeze-drying, or lyophilization within the freezer 32. Freeze-drying of the frozen chitosan biomaterial can be conducted by further cooling the frozen chitosan biomaterial. Typically, a vacuum is then applied. Next, the evacuated frozen chitosan material is subject to ramped heating and/or cooling phases in the continued presence of a vacuum.

In a representative embodiment, following the freezing regime 40, freeze drying conditions are maintained for removing water without collapse of the matrix 12. In a representative embodiment, for example, a prescribed freeze drying temperature, e.g., minus 50° C. is maintained for a preferred time period (e.g., between 1 and 3 hours), while a vacuum, e.g., in the amount of about 170 mTorr, is applied during this time.

Further freeze drying at higher temperatures may be conducted during subsequent drying phases, while maintaining vacuum pressure. The times and temperatures of the drying phase can change depending upon fill volume, mold configuration, lyophilizer capabilities, etc. Step changes are made to keep the matrix temperature below its collapse temperature. The temperature of the matrix 12 is kept as high as possible during the drying phases, but still below the collapse temperature, to provide the shortest cycle time possible. The shelf temperature is ramped up and then down again because high rates of initial sublimation cools the matrix temperature, and as sublimation wanes, matrix temperature increases.

In a representative subsequent primary drying phase, the temperature is (i) ramped over a period of 80 minutes to 30° C., which is then held for 110 minutes; (ii) then lowered over a period of 25 minutes to 14° C., (iii) then further lowered over a period of 180 minutes to minus 6° C., and (iv) then further lowered over a period of 180 minutes to minus 9° C., which is held for a period of 420 minutes. In a representative embodiment subsequent secondary drying phase, the temperature (i) ramped over a period of 120 minutes to 33° C., which is then held for 780 minutes; and (ii) and then lowered back to room temperature (20° C.) and held for a period of 30 minutes.

Figure 18:
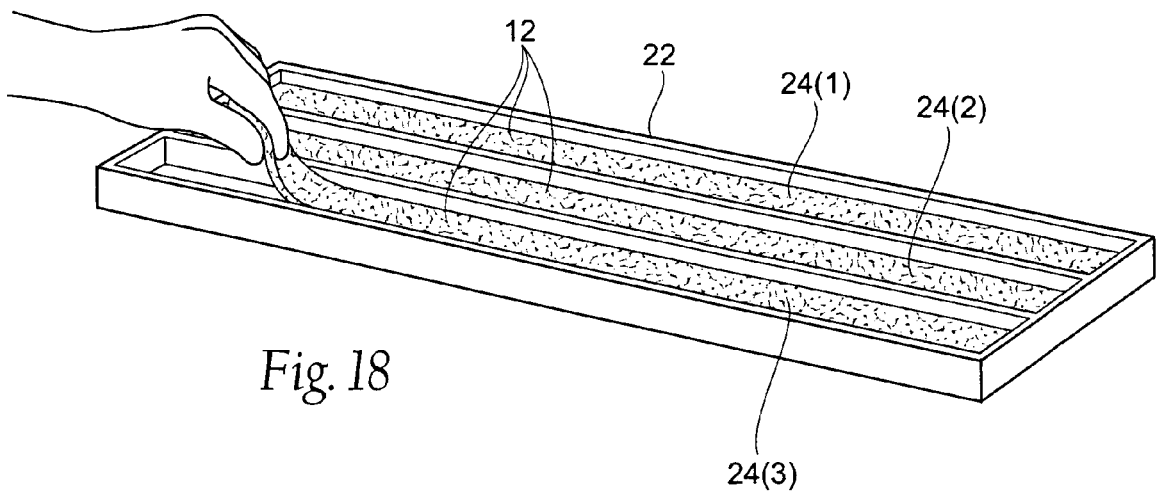
FIG. 18 is a perspective view of the removal of a supple, chitosan matrix structure from the mold after undergoing the freezing regime shown in FIG. 17 as well as a subsequent prescribed freeze-drying process.
Figure 19:
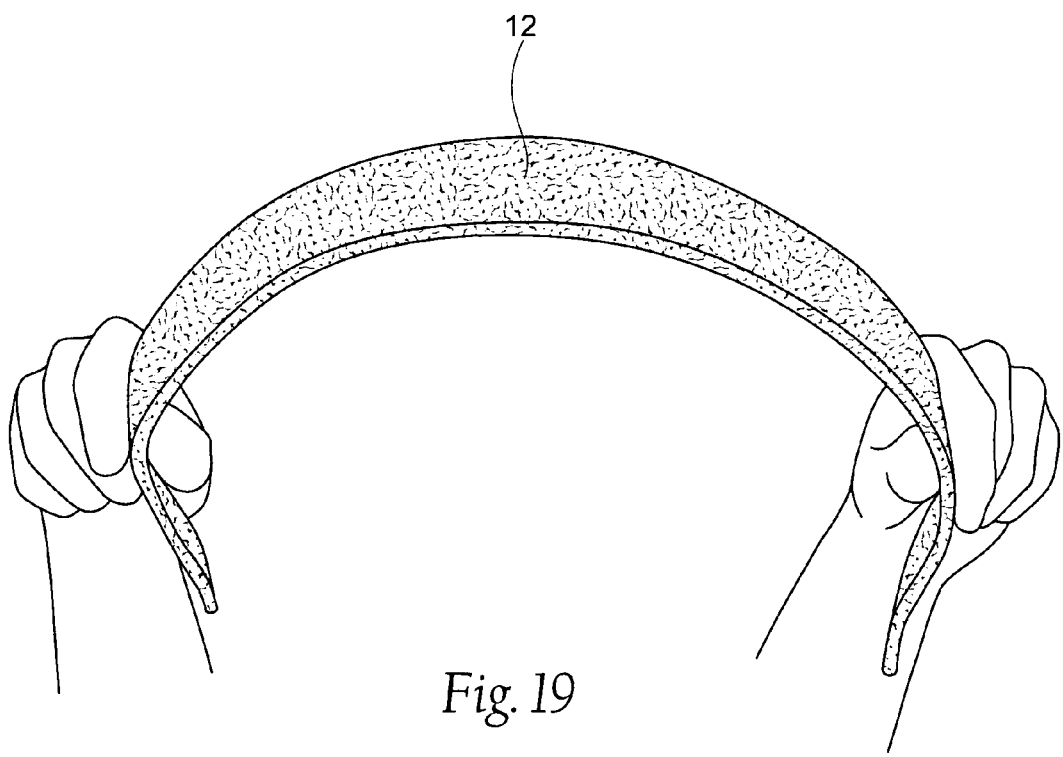
FIG. 19 is a perspective view showing flexure of the supple, chitosan matrix structure after removal from the mold, as shown in FIG. 18.

As shown in FIGS. 18 and 19, the formed, freeze dried matrix 12 can be removed from the mold chamber 24 (1), 24(2), and 24(3). When removed from the mold chamber 24(1), 24(2), and 24(3) (see FIG. 19), the formed, freeze-dried matrix 12 measures 28 inches by 2.75 inches, with a thickness of about 0.23 to 0.28 inches. When removed from the mold (see FIG. 19), the formed matrix 12 exhibits inherently suppleness, i.e., it possesses the inherent flexibility and lack of brittleness and stiffness as described above.

When removed from the mold chamber, the dry chitosan matrix 12 has a density at or near about 0.03 g/cm$^3$ as a result of the freezing regime 40. For purposes of description, this structure will be called an "uncompressed chitosan matrix."

5. Densification of the Chitosan Matrix

In the illustrated embodiment, the uncompressed chitosan matrix (FIG. 19) is desirably subject to a densification process. The densification process increases the density of the uncompressed chitosan matrix to a threshold density greater than or equal to 0.1 g/cm$^3$. It has been observed that a chitosan matrix at or greater than the threshold density do not readily dissolve in flowing blood at 37° C. Following the densification step, the chitosan matrix 12 can be characterized as a supple densified chitosan matrix. A representative target density for the supple, densified chitosan matrix is about 0.1 g/cm$^3$.

Figure 20A:
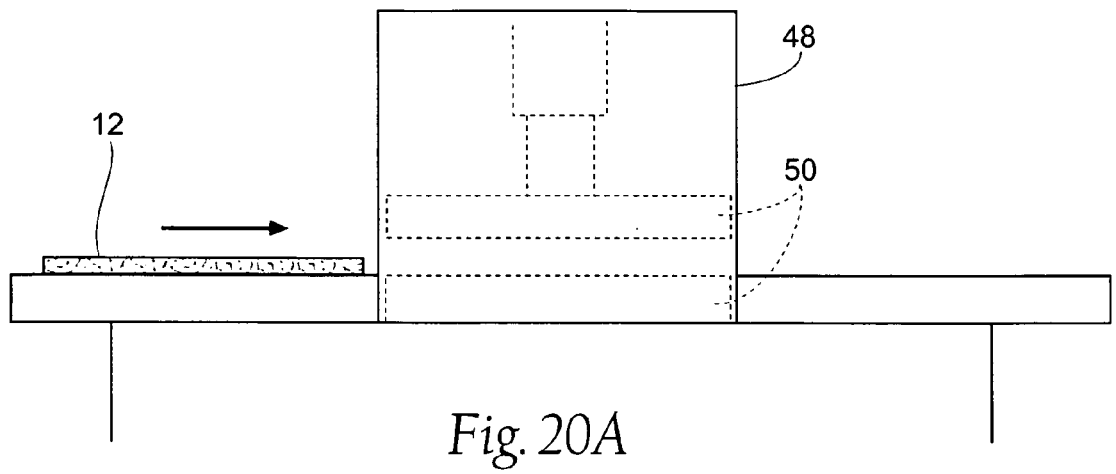
FIGS. 20A, 20B, and 20C show the densification of the supple, chitosan matrix structure shown in FIG. 19, to create a supple, densified chitosan matrix structure.
Figure 20B:
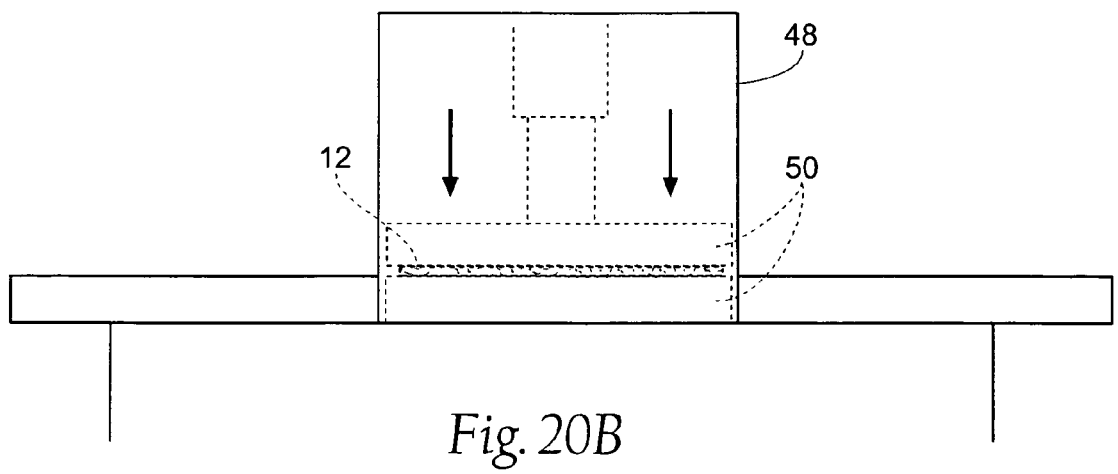
Figure 20C:
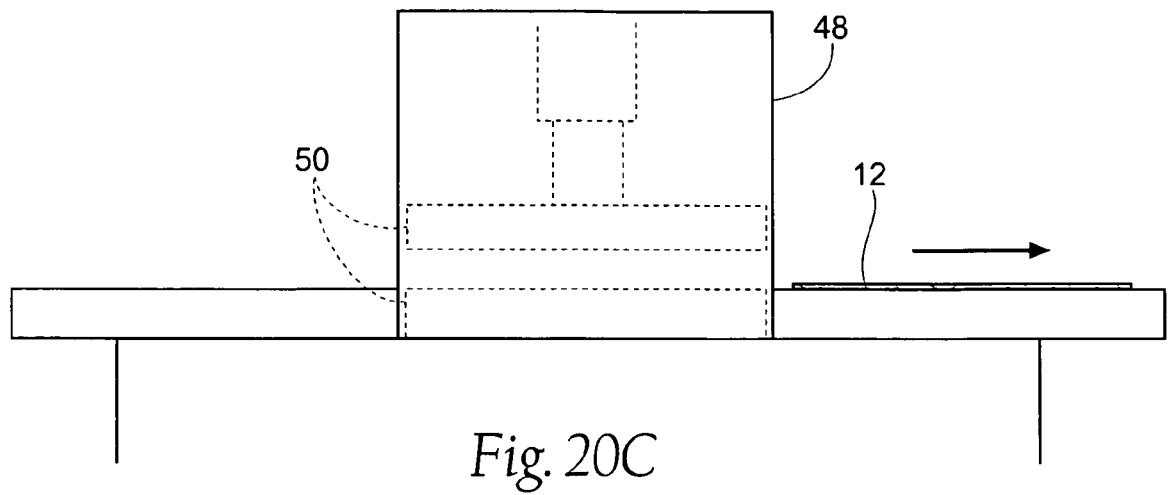

The densification step can be accomplished in various ways. In a representative embodiment (see FIGS. 20A, 20B, and 20C), the uncompressed chitosan matrix (FIG. 20A) is placed inside a compression device 48. Inside the device 48, the uncompressed chitosan matrix 12 is compression loaded between heated platens 50 (FIG. 20B). The compression temperature is preferably not less than about 60° C., more preferably it is not less than about 75° C. and not more than about 85° C.

The compression load of the heated platens 50 reduces the thickness of the uncompressed matrix 12 from about 0.23 to 0.28 inches to about 0.036 inch. The compression load thereby increases the density of the uncompressed matrix from about 0.03 g/cm$^3$ to a target density, e.g., about 0.2 g/cm$^3$. The supple densified chitosan matrix 12 (FIG. 20C) is formed.

It has been observed that the densification process imparts to the densified chitosan matrix 12 significantly increased adhesion strength, cohesion strength and dissolution resistance in the present of blood and liquids.

6. Preconditioning the Densified Chitosan Matrix

Figure 21:
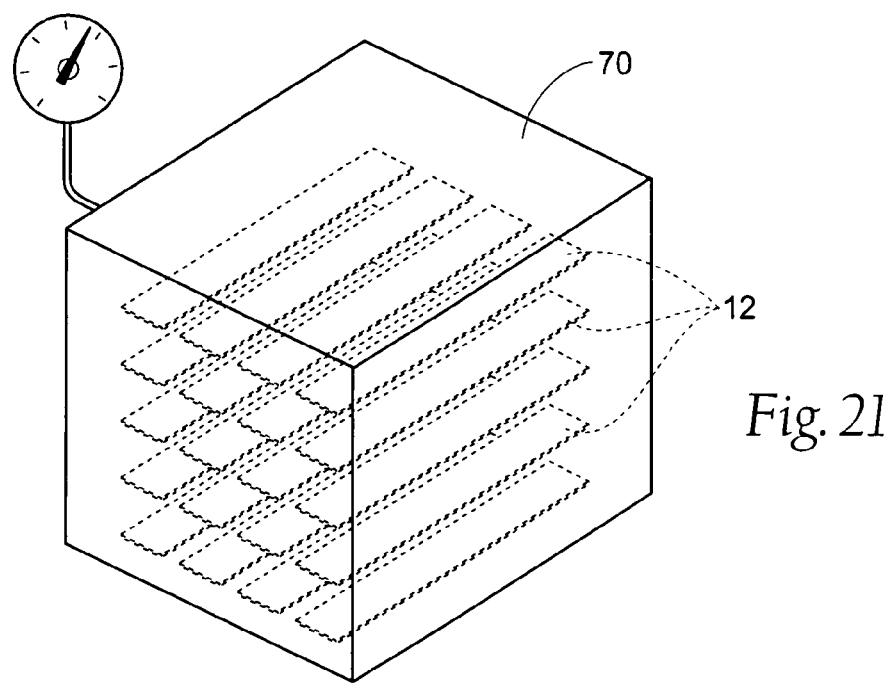
FIG. 21 is a perspective view of an oven which preconditions the supple chitosan matrix structure after densification.

The dry chitosan matrix 12—now densified—is next preferably preconditioned by heating the densified supple chitosan matrix in an oven 70 (see FIG. 21). The oven 70 can be operated at a temperature of preferably up to about 75° C., more preferably to a temperature of up to about 80° C., and most preferably to a temperature of preferably up to about 85° C. Preconditioning is typically conducted for a period of time up to about 0.25 hours, preferably up to about 0.35 hours, more preferably up to about 0.45 hours, and most preferably up to about 0.50 hours. This pre-conditioning step provides further significant improvement in dissolution resistance with a small cost in a 20-30% loss of adhesion properties.

7. Softening of the Densified Chitosan Matrix

Desirably, the conditioned, densified chitosan matrix 12 is subjected to a further softening process, which lends enhanced flexibility and compliance.

The softening process can be accomplished by the use of certain plasticizing agents in solution with the chitosan. However, plasticizing may be problematic, because certain plasticizers can change other structural attributes of the assembly.

For this reason, the softening process is desirably accomplished by the mechanical manipulation of the densified chitosan matrix. The mechanical manipulation can be accomplished in various ways. In a representative embodiment (see FIG. 22) the densified chitosan matrix is passed through a softening device 52.

In the illustrated embodiment (see FIG. 23), the softening device 52 comprises an array of upper and lower rollers 54 and 56. The upper rollers 54 are longitudinally spaced apart along parallel axes. The lower rollers 56 are also spaced apart along parallel axes, which are also parallel to the axes of the upper rollers 54. The lower rollers 56 are further arranged in a staggered relationship relative to the upper rollers 54, such that each lower roller 56 is spaced below and between two spaced apart upper rollers 54 (see FIG. 24), providing an undulating path between the upper and lower rollers 54 and 56. The distance between opposing upper and lower rollers 54 and 56 forming the path is slightly less than the thickness of the densified chitosan matrix.

As a result (see FIG. 24), during passage through the undulating path, the densified chitosan matrix 12 is subject to transverse compression or kneading as well as longitudinal bending along both sides of the matrix 12.

A drive motor 58 (see FIG. 22) is linked by a suitable drive mechanism 60 to the rotate the rollers 54 and 56 (see FIG. 24) to draw the supple densified chitosan matrix 12 through one end of the path and discharge the supple densified chitosan matrix 12 from the opposite end of the path.

Figure 22:
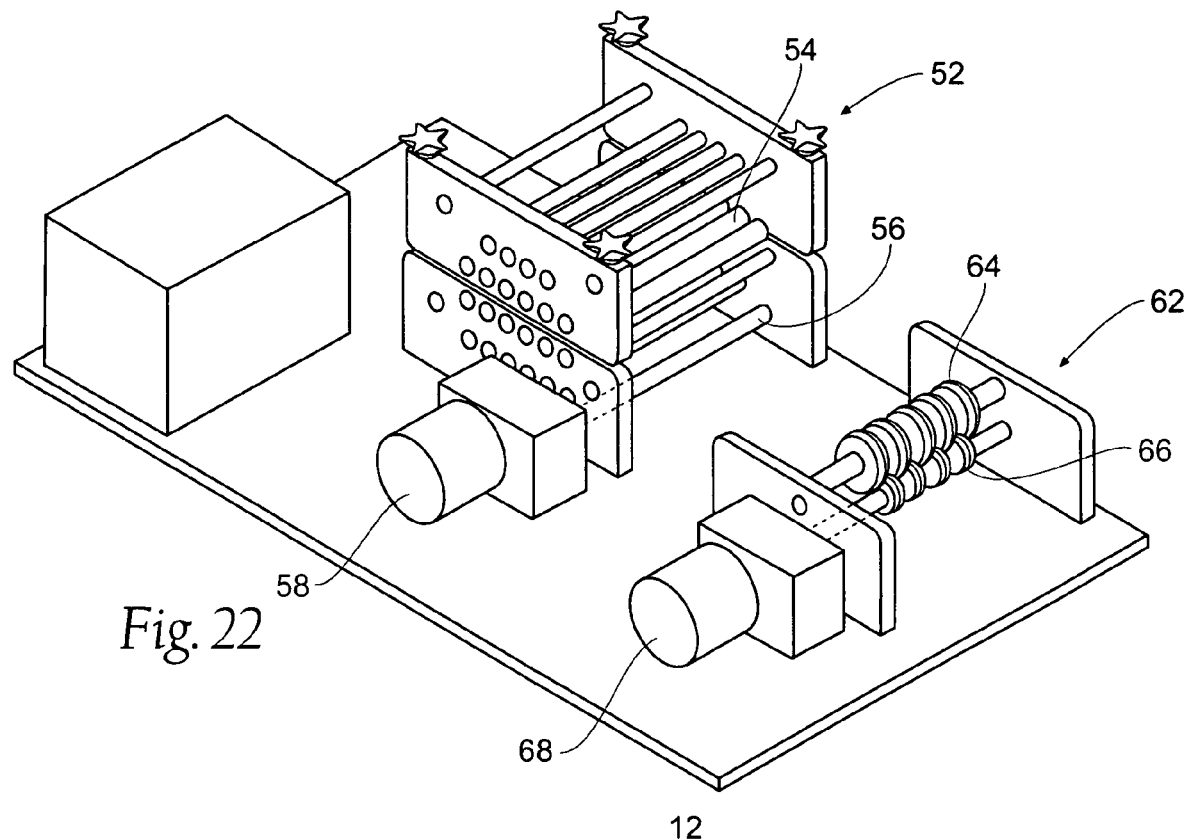
FIG. 22 is a perspective view of a softening machine, which subjects the supple, preconditioned, and densified chitosan matrix structure shown in FIG. 19C to gentle, systematic mechanical softening along its transverse axis (width), which improves its inherent suppleness and compliance.
Figure 23:
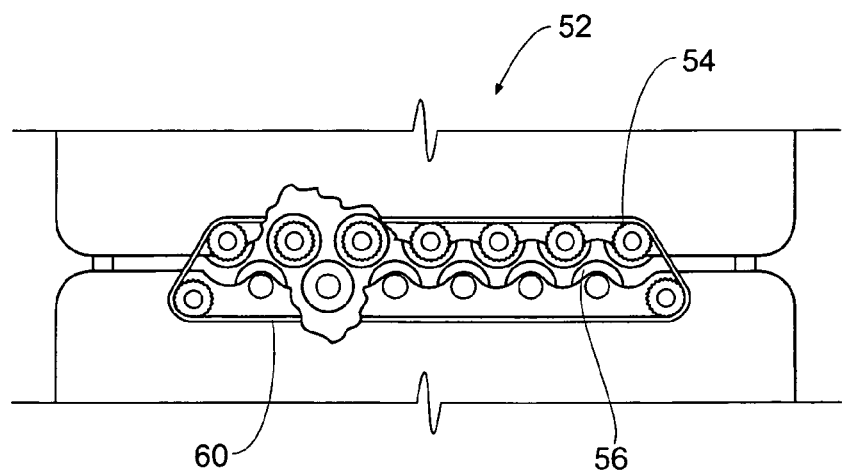
FIG. 23 is a side view of the array of upper and lower rollers that form a part of the softening machine shown in FIG. 22.
Figure 24:
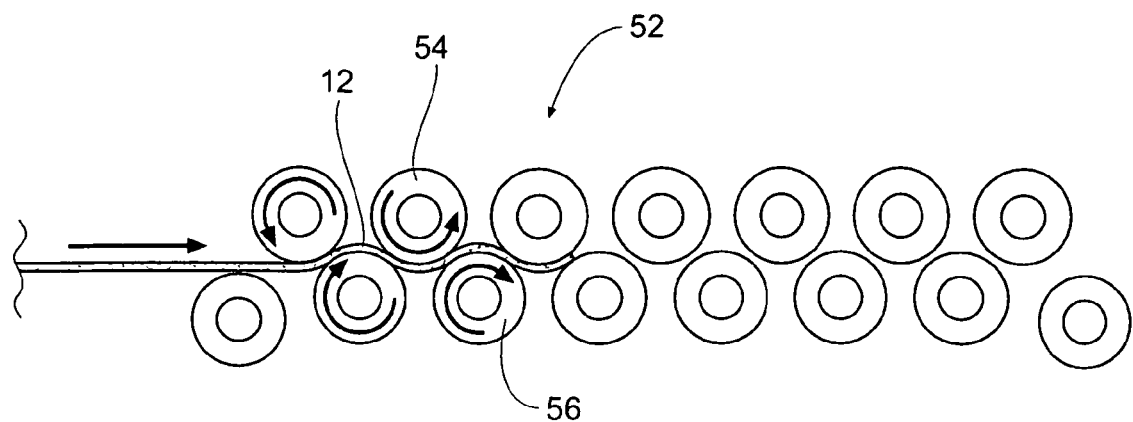
FIG. 24 is a more diagrammatic, side view of the array of upper and lower rollers shown in FIG. 23, with the supple, densified chitsan matrix structure traversing the serpentine path between the upper and lower rollers.
Figure 25:
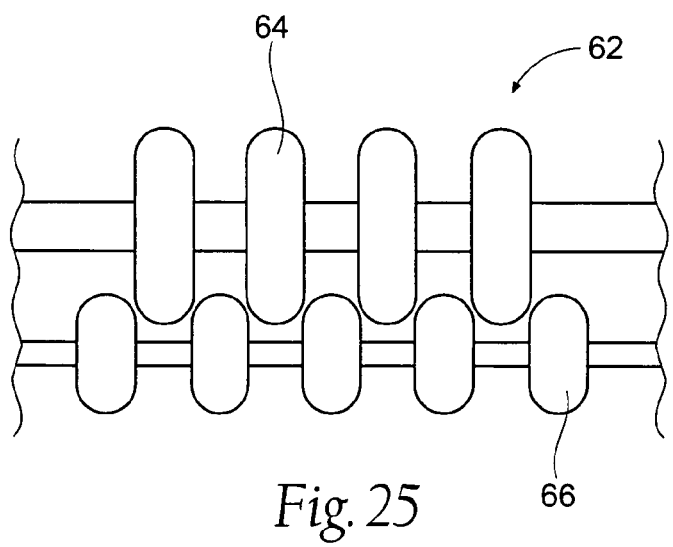
FIG. 25 is a side view of an optional second softening array, which can be arranged either before or after the first array of upper and lower rollers shown in FIGS. 23 and 24, to compress or knead the supple densified chitosan matrix structure along its longitudinal axis.
Figure 26:
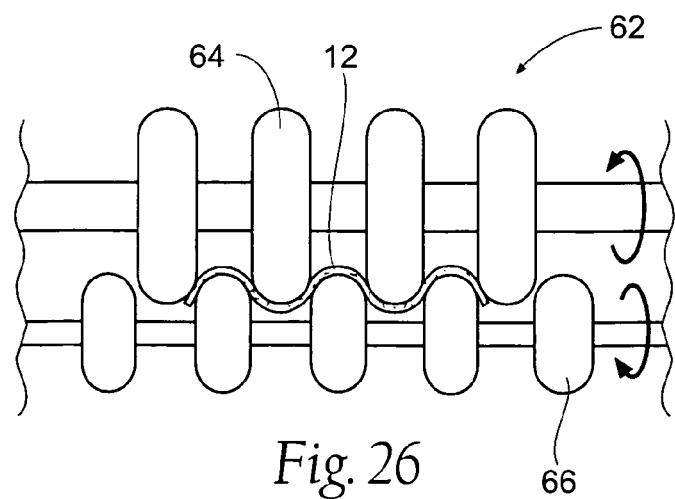
FIG. 26 is a more diagrammatic, side view of the second softening array shown in FIG. 25, with the supple, densified chitsan matrix structure traversing the serpentine path between the upper and lower wheels of the second softening array.

As shown in FIG. 22, the softening device 52, if desired, can further include a second softening array 62, arranged either before or after the first array of upper and lower rollers 54 and 56. The second softening array 62 is sized and arranged to compress or knead the supple densified chitosan matrix 12 along its longitudinal axis, i.e., along the length of the matrix 12 in a direction ninety degrees from the transverse (or width) compression or kneading provided by the first array of upper and lower rollers 54 and 56. In this arrangement (see FIGS. 25 and 26), the second softening array 62 can comprise an upper and lower array of wheels 64 and 66 arranged for rotation about an axis across the width of matrix 12. The upper wheels 64 are spaced apart along the upper axis, and the lower wheels 66 are spaced apart along the lower axis below and between the spaced apart upper wheels 64 (see FIG. 25). The distance between two upper wheels 64 and an intermediate lower wheel 66 is slightly less than the thickness of supple densified chitosan matrix. A drive motor 68 and suitable drive linkage can be provided to draw the supple densified chitosan matrix 12 between the wheels 64 and 66 (see FIG. 26). During passage between the wheels 64 and 66, the supple densified chitosan matrix is subject to compression or kneading along its longitudinal axis.

The softening device 52 provides gentle, systematic mechanical softening of the supple densified chitosan matrix 12. The gentle, systematic mechanical softening of the supple densified chitosan matrix improves its inherent suppleness and compliance, without engendering gross failure of the assembly 10 at its time of use.

The softening device 52 as just described can be used to improve the flexibility and compliance of any hydrophilic polymer sponge structure after manufacture, without loss of beneficial features of robustness and longevity of resistance to dissolution. While the methodologies are described in the context of the supple densified chitosan matrix, it should be appreciated that the methodologies are broadly applicable for use with any form of hydrophilic polymer sponge structure, of which the supple densified chitosan matrix 12 is but one example.

The supple densified chitosan matrix 12 is cut to the form assemblies having the desired shapes and sizes, as shown in FIG. 5.

8. Secure the Backing Layer to the Densified Chitosan Matrix

The backing layer 14 is secured to the chitosan matrix 12 to form the tissue dressing assembly 10. If the backing layer 14 is secured by melt adherence with a top layer of chitosan matrix 12, the backing layer is desirably adhered during the application of heat and pressure during the densification process itself (Step 5 above).

9. Placement in the Pouch

The tissue dressing assembly 10 can he subsequently packaged in the pouch 16, as previously described. The pouch 16 is desirably purged with an inert gas such as either argon or nitrogen gas, evacuated and heat sealed. The pouch 16 acts to maintain interior contents sterility over an extend time (at least 24 months) and also provides a very high barrier to moisture and atmospheric gas infiltration over the same period.

10. Sterilization

After pouching, the tissue dressing assembly 10 is desirably subjected to a sterilization step. The tissue dressing assembly 10 can be sterilized by a number of methods. For example, a preferred method is by irradiation, such as by gamma irradiation, which can further enhance the blood dissolution resistance, the tensile properties and the adhesion properties of the wound dressing. The irradiation can be conducted at a level of at least about 5 kGy, more preferably a least about 10 kGy, and most preferably at least about 15 kGy.

11. Incorporation of Therapeutic Agents

One or more therapeutic agents can be incorporated into the chitosan matrix 12, e.g., either before or after the freezing step, and before the drying and densification steps. The rate at which the therapeutic agents are released from the matrix can be controlled by the amount of densification. The more densified the hydrophilic polymer sponge structure is made to be, the slower will be the rate of release of the therapeutic agent incorporated into the structure.

Examples of therapeutic agents that can be incorporated into the chitosan matrix 12 include, but are not limited to, drugs or medications, stem cells, antibodies, anti-microbials, anti-virals, collagens, genes, DNA, and other therapeutic agents; hemostatic agents like fibrin; growth factors; platelet polyphosphate, and similar compounds.

EXAMPLE 1

Sealing Renal Parenchymal Wound Following Laproscopic Partial Nephrectomy

Nephron sparing surgery (NSS) has become a standard treatment in patients with a compromised contralateral kidney or in select patients with a favorably located, small renal tumor with a normal contralateral kidney.

While minimally invasive surgery is becoming established for radical nephrectomy, similar approach for nephron sparing surgery have been limited largely due to technical issues such as achieving adequate renal parenchymal hemostasis, and secure caliceal closure. Due to these technical difficulties associated with minimally invasive approach the current complication rates related to urinary leakage and hemorrhage following laparoscopic partial nephrectomy (LPN) remains significantly higher than the open NSS.

At present time, LPN remains technically challenging due to, lack of a reliable method for obtaining consistent parenchymal hemostasis, and the technical difficulties in obtaining secure suture closure of the renal collecting system. Various topical sealants including fibrin glue, gelatin resorcinol formaldehyde glue, and oxidized cellulose or gelfoam sponges are frequently used alone or in conjunction with specialized instrumentation and agents to assist hemostasis. However, these topical preparations mostly require renal hilar vascular control during the application and are unable to seal urinary collecting system effectively. Moreover, the currently topical preparations are mostly composed of heterogenic protein, which may bear a potential risk of severe allergic reaction and possible viral contamination.

An absorbable tissue dressing assembly 10 comprising a chitosan matrix 12 frozen, freeze dried, densified, and softened, as described herein) with a poly-4-hydroxy butyrate backing layer 14 (TephaFlex™ Material manufactured by Tepha Inc) (the "chitosan hemostatic dressing") was evaluated for renal parenchymal wound sealing to control hemorrhage and urine leakage in laparoscopic partial nephrectomy (LPN). The chitosan hemostatic dressings used were 58 mm in diameter and between 1.5 mm to 1.85 mm thick with a density, after densification, of between 0.12 g/cm$^3$ and 0.15 g/cm$^3$. The poly-4-hydroxy butyrate backing layer 14 was 25-μm thick. The backing side faces up on application and the other side, or "active side", is the side directly applied to the wound surface.

Forty-five LPN were performed on twenty-four domestic swine. After excision of the lower pole of the kidney, either the chitosan hemostatic dressing (N=24) was applied to seal the wound, or conventional suture technique (N=21) (the control group) was used to control bleeding. The operative parameters included estimated blood loss (EBL) and operative time (OT) were recorded. The animals were euthanized at 1 hour, 3 days and 7 days postoperatively. Retrograde ureteropyelography was performed to assess the urine leakage.

All animals achieved initial hemostasis and survived with both treatments. Mean EBL was significantly lower when the chitosan hemostatic dressing was used, when compared to it in the control group (128 ml EBL for the chitosan hemostatic dressing vs. 363 ml EBL for the control group, p=0.04).

There was no significant difference in OT between the two treatments.

In the control group, all kidneys present urine leakage after LPN in both acute and chronic periods. In the chitosan group, 8% (1/12) of kidneys had acute urine leakage, 33% of them developed small urinoma at postoperative day 3 and 7, respectively. Histopathological analysis showed similar and mild informatory responses in both groups.

The chitosan-based hemostatic dressing proved effective as a primary or supplemental treatment for sealing the parenchymal wound in laparoscopic partial nephrectomy in the animal model.

EXAMPLE 2

Use of a Chitosan-Based Hemostatic Dressing in Laproscopic Partial Nephrectomy

An absorbable tissue dressing assembly 10 comprising a chitosan matrix 12 frozen, freeze dried, densified, and softened, as described herein) with a poly-4-hydroxy butyrate backing layer 14 (TephaFlex™ Material manufactured by Tepha Inc) (the "chitosan hemostatic dressing") was evaluated for renal parenchymal wound sealing to control hemorrhage and urine leakage by sealing off the renal parenchymal wound surface in LPN procedures.

The chitosan hemostatic dressings used were 58 mm in diameter and between 1.5 mm to 1.85 mm thick with a density, after densification, of between 0.12 $g/cm^3$ and 0.15 $g/cm^3$. The poly-4-hydroxy butyrate backing layer 14 was 50-μm thick. The backing side faces up on application and the other side, or "active side", is the side directly applied to the wound surface.

Nine heparinized domestic swine underwent bilateral laparoscopic partial nephrectomies involving either a polar (N=13) or wedge resection (N=5) followed by treatment with the chitosan hemostatic dressing. Estimated blood loss, hemostatic score, urinary leakage, operative time and adhesion score of the chitosan dressing were recorded.

After induction of general anesthesia, all the procedures were performed under general anesthesia with intubation using strict aseptic precautions. The animal was placed in a lateral position and CO2 pneumoperitoneum was created using a 14-gauge Veress needle. Two 10 mm and two 5 mm ports were placed. A bolus of 5000 units of intravenous heparin was given 10 minutes prior to operation and additional bolus dosages of 1000 units were given intraoperatively every 30 minutes as required in order to maintain the activated clotting time (ACT) over 200 seconds and rechecked throughout the surgical procedure. ACT was rechecked every 30 minutes. If ACT dropped below 200 additional 1000 units of heparin were re-given until it was above 200.

The kidney was identified and following exposure of renal hilum both the poles were completely mobilized. Either an upper or a lower polar, or a wedge resection was performed using a harmonic scalpel (Ethicon Endosurgery, Cincinnati, Ohio) without hilar occlusion. In the polar resection, at least one third of renal tissue was resected; in the wedge resection, an approximate 3 cm in depth and 3 cm in width tissue was removed from middle of kidney, which making sure the collecting system was entered by visual confirmation. The hemorrhage through the parenchymal surface of the kidney was assessed visually by assigning a 0-4 hemostatic score (0=no hemostasis; 1=steady bleeding; 2=moderate bleeding; 3=mild oozing; and 4=dry).

An appropriate sized piece of chitosan dressing was delivered through a 10-mm port and deployed onto the resected surface for 3 minutes with gentle compression using a 10-mm fan retractor (Endo Retract, Auto Suture☐, U.S Surgical, Norwalk, Conn.). Hemostatic score was recorded again. The ability of the dressing to adhere securely to the entire cut surface of the renal parenchyma was assessed on a numeric scale of 0-5 (0=no adhesive; 1=weakly adhering to one small portion of surface; 2=uniformly but weakly adhering to whole surface; 3=general weak with some moderate adherence; 4=limited but strong local adherence; and 5=uniform strong adherence). In case of non or incomplete adherence of the dressing to the renal parenchyma the dressing was removed and a second piece was deployed. The numbers of attempts required for successful deployment were recorded. After completion of satisfactory hemostasis and secure adhesion of the dressing on one side, the animal was turned onto the contralateral side and the procedure was repeated.

Once both sides had achieved initial hemostasis, the abdomen was deflated and additional 30 minutes were given to observe the stability of the repairs. Pneumoperitoneum was reestablished and the repair sites were reassessed laparoscopically for any evidence of rebleeding or urinary extravasation and to obtain the final hemostatic score. A retrograde pyelography was performed to assess the integrity of the collecting system and pyelocaliceal urinary leakage via bilateral ureteral catheterization under cystotomy. Finally the animals were euthanized and both kidneys were removed through midline laparotomy for gross assessment of the quality of adhesion of the dressing. A thumbprint of the resected portion of the kidney was obtained on a graph paper to determine the area of resection.

Of 18 procedures, 17 achieved complete hemostasis after deployment of the chitosan hemostatic dressing. The hemostasis score improved significantly after the deployment in both polar ($p<0.001$) and wedge ($p=0.017$) resections. The rate of successful pyelocaliceal sealing was 85% (11/13) in polar and 60% (3/5) in wedge resections.

The chitosan hemostatic dressing is effective as a primary or supplemental material for controlling parenchymal hemorrhage and sealing the renal collecting system following LPN in the animal model.

Due to characteristic physical properties of chitosan hemostatic dressing, secure application of this material is feasible and technically less challenging following LPN. For the best result it is necessary to hold the dressing firmly and steady against the wound surface of renal resection for approximately 3 minutes during the operation.

In the case of polar resection, this goal is easily accomplished with commercially available fan-type retractor. All of the polar resections achieved complete hemostasis with this technique (100%, 13/13) within a reasonably short duration of time.

Closure of pyelocalceal system traditionally requires watertight suture closure. Laparoscopically this task is technically challenging and time consuming. The ability of the chitosan hemostatic dressing to adhere strongly to the freshly incised raw surface of the solid organs provides a unique opportunity to seal the pyelocalceal system. The chitosan hemostatic dressing was able to seal the pyelocalceal system securely without any evidence of urinary leakage on follow-up retrograde pyelography in majority (85%, 11/13) of the polar resections. The success rate was about the same or better than that reported with traditional techniques.

In the case of wedge resections, the amount of blood loss and the number of attempts required to apply the dressing were relatively greater. Also the quality of adhesion of the chitosan hemostatic dressing to the freshly incised renal parenchyma was poorer leading to worse hemostatic scores and higher rate of urinary leakage (2/5, 40%). Typically, application of the chitosan hyemostatic dressing via laparoscopic approach in wedge resections is more technically challenging due to the awkward V-shape configuration of the renal parenchymal injury and a lack of appropriate instruments that would allow maintenance of firm and uniform firm pressure over the dressing for three minutes (the minimum desired time for achieving secure adhesion of the dressing). Further developments are required to improve instrumentation for the deployment of the chitosan dressing in laparoscopic wedge resections.

The chitosan hemostatic dressing provides an easy and rapid method to control bleeding and seal the parenchymal wound surface. Use of the chitosan dressing can simplify LPN procedure to save operative time, and it can be used without hilar vascular occlusion to avoid renal warm ischemia. Clinical situations for possible use of the chitosan dressing in laparoscopic surgery are numerous. Bleeding from visceral organs after routine biopsy and resection, portal bleeding, or more severe bleeding from hilar vascular injury, and surgical bleeding from coagulopathy patients can be controlled using the chitosan hemostatic dressing as well.

This example presents promising results for achieving immediate hemostasis and sealing urinary leakage with the use of the chitosan hemostatic dressing following laparoscopic polar or wedge resection of the kidney in a porcine model. The technique is technically less demanding and allows rapid control of hemorrhage and sealing of severed pyelocaliceal system. The technique also has several potential applications including laparoscopic control of hemorrhage form solid organs as a result of surgical injury or following trauma.

III. Conclusion

It should be apparent that above-described embodiments of this invention are merely descriptive of its principles and are not to be limited.

We claim:

1. An absorbable tissue dressing assembly comprising
   a tissue dressing matrix including an absorbable hydrophilic polymer material;
   a flexible absorbable polymer film or mesh backing layer including at least one of absorbable aliphatic polyesters, aliphatic polyurethanes, hyaluronic acid, a hyaluronate, and a poly-hydroxyl butyrate material; and
   wherein the backing layer includes at least one of a woven nano-fiber material and a woven micro-fiber material.

2. An assembly according to claim 1
   wherein the absorbable hydrophilic polymer material comprises a chitosan material.

3. An assembly according to claim 2
   wherein the backing layer is bonded by direct adhesion with a top layer of the absorbable hydrophilic polymer material.

4. An assembly according to claim 1
   wherein the tissue dressing matrix includes spherulitic nucleated structures within a lamella structure.

5. A method of manufacturing an absorbable tissue dressing assembly as defined in claim 4 comprising the following steps:
   subjecting a solution of a chitosan hydrophilic polymer to phase separation by a controlled freezing process that includes a delay interval, followed by a controlled freeze-drying or lyophilization water removal step that occurs at a temperature below the collapse temperature to create the tissue dressing matrix; and
   subjecting the tissue dressing matrix, after freeze-drying or lyophilization to a densification process.

6. An assembly according to claim 1
   wherein the backing layer presents an increased surface area that can accelerate biodegradation.

7. An assembly according to claim 1
   wherein the tissue dressing matrix is sized and configured to define a perimeter edge, and the backing layer is sized and configured to extend beyond the perimeter edge to present a skirt of material to receive suture material or staples.

8. An assembly according to claim 1
   wherein the tissue dressing matrix is sized and configured to define an elongated strip having opposite ends, so that the elongated strip can be wrapped around a site, and wherein the backing layer is placed at one opposite end of the elongated strip.

9. An assembly according to claim 8
   wherein the site is a blood vessel and the elongated strip can be wrapped around the blood vessel without collapsing the vessel on itself.

10. A method comprising
    providing an absorbable tissue dressing assembly as defined in claim 1; and
    performing a laparoscopic procedure using the absorbable tissue dressing assembly.

11. A method according to claim 10
    wherein the laparoscopic procedure includes at least one of an abdominal aortic aneurysmectomy; spleen, liver, kidney, or gallbladder surgeries; open heart and bypass procedures; hysterectomies; total joint arthoplasties, burns and face lifts; radical neck dissections; trauma such as gun shot, knife wounds, wound debridement; spinal fusions and laminectomies; bowel and colon resections; radial prostatectomies; vascular anastomoses; and laparoscopic nephrectomies.

* * * * *

UNITED STATES PATENT AND TRADEMARK OFFICE
CERTIFICATE OF CORRECTION

PATENT NO. : 8,269,058 B2  Page 1 of 1
APPLICATION NO. : 12/218568
DATED : September 18, 2012
INVENTOR(S) : McCarthy et al.

It is certified that error appears in the above-identified patent and that said Letters Patent is hereby corrected as shown below:

In the Specifications:

Column 1, line 29    Before "Field of the Invention" insert
--GOVERNMENT RIGHTS
This invention was made with government support under Contract DAMD 17-02-C-0095 awarded by U.S. Army Medical Materiel Development Activity. The government has certain rights in the invention.--

Signed and Sealed this
Seventh Day of May, 2013

Teresa Stanek Rea
*Acting Director of the United States Patent and Trademark Office*